United States Patent
Gervay-Hague et al.

(10) Patent No.: US 10,100,074 B2
(45) Date of Patent: Oct. 16, 2018

(54) REGIOSELECTIVE SILYL EXCHANGE OF PER-SILYLATED OLIGOSACCHARIDES

(71) Applicant: THE REGENTS OF THE UNIVERSITY OF CALIFORNIA, Oakland, CA (US)

(72) Inventors: Jacquelyn Gervay-Hague, Davis, CA (US); Matthew Schombs, Oxford (GB)

(73) Assignee: The Regents of the University of California, Oakland, CA (US)

(*) Notice: Subject to any disclaimer, the term of this patent is extended or adjusted under 35 U.S.C. 154(b) by 51 days.

(21) Appl. No.: 14/975,537

(22) Filed: Dec. 18, 2015

(65) Prior Publication Data

US 2016/0176909 A1    Jun. 23, 2016

Related U.S. Application Data

(63) Continuation of application No. PCT/US2014/043006, filed on Jun. 18, 2014.

(60) Provisional application No. 61/836,828, filed on Jun. 19, 2013.

(51) Int. Cl.
| | |
|---|---|
| *C07H 23/00* | (2006.01) |
| *C07H 13/04* | (2006.01) |
| *C07H 3/06* | (2006.01) |

(52) U.S. Cl.
CPC .............. *C07H 13/04* (2013.01); *C07H 3/06* (2013.01); *C07H 23/00* (2013.01); *Y02P 20/55* (2015.11)

(58) Field of Classification Search
None
See application file for complete search history.

(56) References Cited

U.S. PATENT DOCUMENTS

| | | | |
|---|---|---|---|
| 5,514,659 A | 5/1996 | Petiton et al. | |
| 2011/0166078 A1 | 7/2011 | Cabannes et al. | |
| 2012/0220759 A1 | 8/2012 | Seifert et al. | |
| 2015/0152462 A1† | 6/2015 | Huang | |

FOREIGN PATENT DOCUMENTS

| | | | | |
|---|---|---|---|---|
| EP | 0772618 B1 | 4/2002 | | |
| EP | 1905838 A1 | 4/2008 | | |
| EP | 2138586 A1 | 12/2009 | | |
| WO | 01/38337 A2 | 5/2001 | | |
| WO | 2004/005308 A2 | 1/2004 | | |
| WO | WO2011/030160 | * | 3/2011 | ........... A61K 31/351 |
| WO | 2012/101605 A1 | 8/2012 | | |
| WO | 2014/205115 A2 | 12/2014 | | |

OTHER PUBLICATIONS

Lay et al., "A simple access to lactose-derived building blocks required in glycoconjugate synthesis" Carbohydrate Research (1997) vol. 303 pp. 39-49.*
Ruhela et al., "Efficient synthesis of the antigenic phosphoglycans of the Leishmania parasite" Chemical Communications (2001) pp. 2024-2025.*
Jiang et al., "Synthesis and structure-activity relationships studies of brartemicin analogs as anti-invasive agents" The Journal of Antibiotics (2013) vol. 66 pp. 531-537.*
Gensler et al., "Trehalose Covalently Conjugated to Bovine Serum Albumin" Journal of Organic Chemistry vol. 42 No. 1 pp. 130-135 (Year: 1977).*
Witschi et al., "Selective Acetylation of per-O-TMS-Protected Monosaccharides," American Chemical Society, Org. Lett., 2010, vol. 12, No. 19, pp. 4312-4315.
International Application No. PCT/US2014/043006, "International Search Report and Written Opinion", dated Dec. 10, 2014, 11 pages.

\* cited by examiner
† cited by third party

*Primary Examiner* — Eric Olson
(74) *Attorney, Agent, or Firm* — Kilpatrick Townsend and Stockton LLP

(57) ABSTRACT

The present invention provides novel, regioselectively-acylated oligosaccharide compounds and methods for preparing them. In another aspect, the. invention provides a method for preparing a selectively-acylated oligosaccharide. The method includes forming a reaction mixture containing a protected oligosaccharide and an acylating agent. The protected oligosaccharide includes at least three hydroxyl moieties and each hydroxyl moiety is protected with a silyl protecting group. The reaction mixture is formed under conditions sufficient to selectively replace at least one silyl protecting group with a —C(0)-C1_6 alkyl group, and the selectively-acylated oligosaccharide comprises at least one —C(0)-C1_6 alkyl group and at least one silyl protecting group.

2 Claims, 5 Drawing Sheets

REGIOSELECTIVE SILYL EXCHANGE OF PER-SILYLATED OLIGOSACCHARIDES

CROSS-REFERENCES TO RELATED APPLICATIONS

This application is a continuation of International Patent Application No. PCT/US2014/043006, filed Jun. 18, 2014, which claims priority to U.S. Provisional Patent Application No. 61/836,828, filed Jun. 19, 2013, which applications are incorporated herein by reference in their entirety.

STATEMENT AS TO RIGHTS TO INVENTIONS MADE UNDER FEDERALLY SPONSORED RESEARCH AND DEVELOPMENT

This invention was made with Government support under Grant No. GM090262, awarded by the National Institutes of Health; and Grant Nos. 9724412 and CHE9808183, awarded by the National Science Foundation. The Government has certain rights in this invention.

BACKGROUND OF THE INVENTION

Lactose is a core structural unit of many complex carbohydrates including the globo series of tumor associated carbohydrate antigens (TACAs). Globotriaosyl ceramide (Gb3), Gb5, and Globo-H all share the structural feature resulting from galactosylation of the 4' hydroxyl of lactose giving rise to $P^k$ trisaccharide (FIG. 1). The carbohydrate backbone of $P^k$ trisaccharide has attracted the attention of synthetic chemists since most, if not all, syntheses of the globo series intercept variously protected versions of the trisaccharide at some point during the synthesis. Nicolaou and co-workers were the first to report the synthesis of Gb3, and their approach remains one of the most efficient to date. A total of eleven steps (from commercially available lactose) were required to prepare a protected version of $P^k$ trisaccharide that served as a donor for the ceramide aglycone. Seven of those steps were focused on orthogonally protecting lactose for 4' galactosylation. In fact, all previously reported chemical syntheses of $P^k$ trisaccharide require between 6-12 steps to prepare the lactosyl acceptor.

Recently, the present inventors demonstrated that per-O-silylated monosaccharides undergo regioselective exchange of silicon for acyl protecting groups providing useful building blocks for organic synthesis in a single step. This process not only results in the generation of orthogonally protected carbohydrates, but also circumvents the well-documented problem of trans-acetylation associated with partially acylated pyranosides. While selective acetylation of the primary C-6 hydroxyl of alkyl glycosides has been demonstrated, preferential modification of other hydroxyl groups is more challenging. Unfunctionalized carbohydrates have proven even more difficult to selectively modify, as they can exhibit anomalous behaviour. As opposed to using either alkyl glycosides or unfunctionalized sugars, the present invention is based on the selective exchange of silyl ether moieties in protected disaccharides with acyl moieties. Surprisingly, the exchange can be achieved under conditions that would otherwise have been expected to result in glycosidic cleavage of the disaccharide substrates. This extraordinary reactivity allows for the rapid preparation of carbohydrate derivatives such as orthogonally 4'-protected lactose, which can be readily transformed into $P^k$ trisaccharide. As such, the invention meets a long-standing need for synthetic intermediates that can be used for the preparation of biologically and industrially important carbohydrate compounds.

BRIEF SUMMARY OF THE INVENTION

In one aspect, the invention provides a compound according to Formula I:

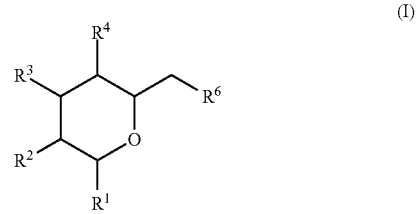

(I)

or an isomer thereof, wherein $R^1$, $R^2$, $R^3$, $R^4$, and $R^6$ are each independently selected from hydrogen, —$OR^7$, an α-linked monosaccharide, and a β-linked monosaccharide. The monosaccharide has a structure according to Formula II:

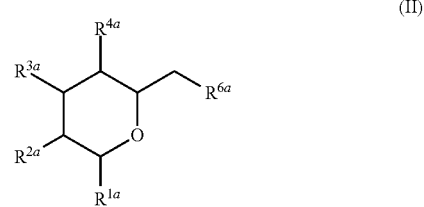

(II)

wherein $R^{1a}$, $R^{2a}$, $R^{3a}$, $R^{4a}$, and $R^{6a}$ are each independently selected from hydrogen, —$OR^7$, and a linking moiety —O—. The linking moiety links the monosaccharide to the moiety according to Formula I. In compounds of Formula I, each $R^7$ is independently selected from hydrogen, —C(O)—$C_{1-6}$alkyl and —Si($R^8$)$_3$; and each $R^8$ is independently selected from $C_{1-6}$ alkyl and $C_{6-10}$ aryl. Only one of $R^1$, $R^2$, $R^3$, $R^4$, and $R^6$ is the monosaccharide; at least one of $R^1$, $R^2$, $R^3$, $R^4$, and $R^6$ is —$OR^7$, wherein $R^7$ is —C(O)—$C_{1-6}$ alkyl; and at least one of $R^1$, $R^2$, $R^3$, $R^4$, $R^6$, $R^{1a}$, $R^{2a}$, $R^{3a}$, $R^{4a}$, and $R^{6a}$ is —$OR^7$, wherein $R^7$ is selected from hydrogen and —Si($R^8$)$_3$.

In another aspect, the invention provides a method for preparing a selectively-acylated oligosaccharide. The method includes forming a reaction mixture containing a protected oligosaccharide and an acylating agent. The protected oligosaccharide includes at least three hydroxyl moieties and each hydroxyl moiety is protected with a silyl protecting group. The reaction mixture is formed under conditions sufficient to selectively replace at least one silyl protecting group with a —C(O)—$C_{1-6}$ alkyl group, and the selectively-acylated oligosaccharide comprises at least one —C(O)—$C_{1-6}$ alkyl group and at least one silyl protecting group.

In some embodiments, the selectively acylated oligosaccharide is a compound according to Formula I as described above.

DETAILED DESCRIPTION OF THE INVENTION

I. General

Figure 1:
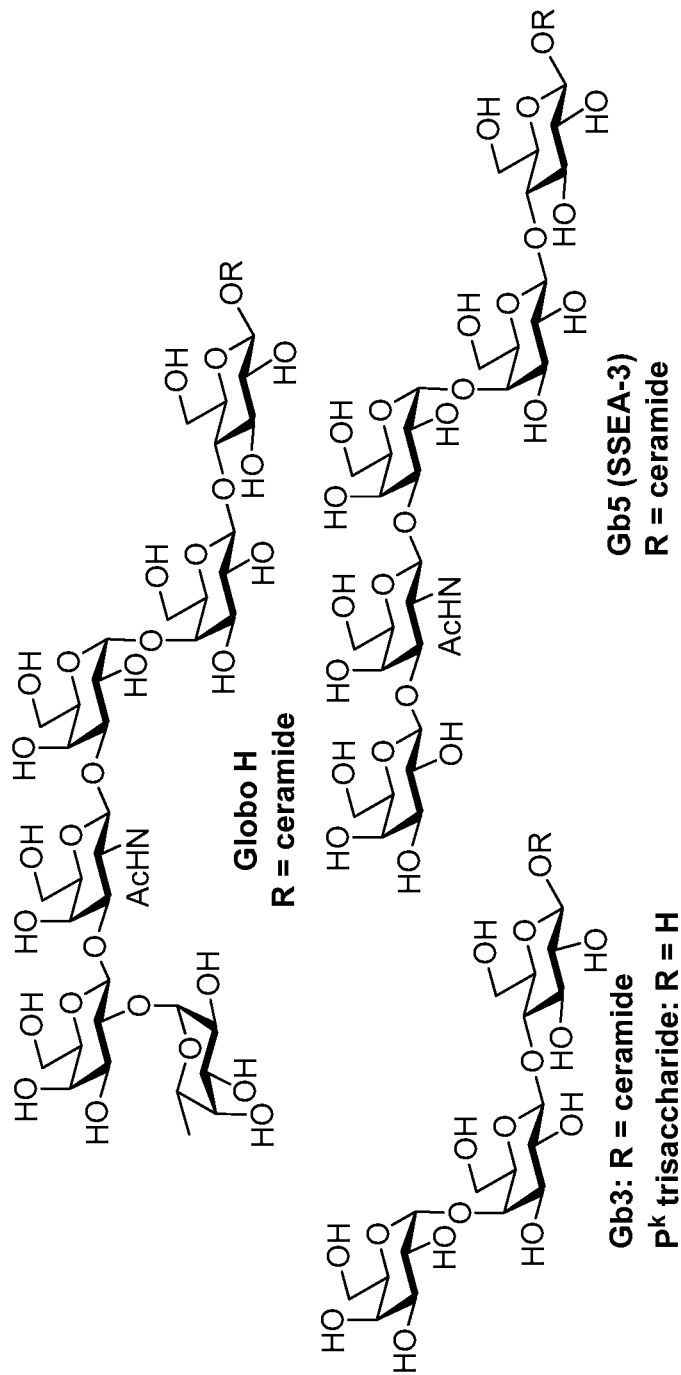
FIG. 1 shows common tumor associated carbohydrate antigens (TACAs).

The invention is based on the surprising discovery that O-silylated disaccharides undergo regioselective exchange of silyl for acyl protecting groups when treated with selected acylating agents without cleavage of the glycosidic bond. Regiocontrol is achieved by limiting the equivalents of acid used in the reaction, and microwave irradiation hastens the process. The reaction conditions can be applied to glucose- and galactose-containing disaccharides, such as lactose, melibiose, cellobiose and trehalose as well as other disaccharide substrates.

Surprisingly, the reaction conditions do not cause glycosidic cleavage of the disaccharide substrates as might be expected. The internal glycosidic linkages of these reactive disaccharides can be susceptible to cleavage under a variety of reaction conditions, limiting the scope of transformations that can be successfully performed on them. For example, immediate cleavage of the internal glycosidic linkage of per-O-TMS-melibiose has been observed upon addition of TMSI, even at 0° C. (Bhat, A., et al. *Org. Lett.* 2001, 3 (13), 2081-2084). Other persilylated disaccharides, such as per-O-TMS-cellobiose and per-O-TMS-lactose, are known to be stable only to a brief exposure to TMSI. Furthermore, microwave conditions have been employed for the degradation of oligosaccharides and polysaccharides (Hu, T., et al., *Carbohydr. Res.* 2013, 373 (O), 53-58). Moreover, unprotected disaccharides are far less soluble in most organic solvents than the monosaccharides that they are composed of. Taken together, these challenges make disaccharides ideal substrates for the technology.

The unexpected stability of the glycosidic bond in the present invention facilitates the synthesis and functionalization of a wide variety of complex glycoconjugates. Glycolipids, glycodendrimers and glycopeptides containing disaccharides, trisaccharides and tetrasaccharides are widely regarded important synthetic targets. In addition to their use as multivalent scaffolds and glycosyl donor precursors, selectively acetylated disaccharides can also function as glycosyl acceptors. In this manner, these bifunctional intermediates are poised to serve as modular building blocks for more complex oligosaccharides, such as members of the globo series. The use of selectively functionalized donors and acceptors allows for increased diversity at each step.

II. Definitions

As used herein, the term "monosaccharide" refers to a sugar having a six-membered carbon backbone (i.e., a hexose). Examples of monosaccharides include, but are not limited to, glucose (Glc), galactose (Gal), mannose (Man), glucuronic acid (GlcA), and iduronic acid (IdoA). Monosaccharides also include hexoses substituted with hydroxy groups, oxo groups, amino groups, acetylamino groups, and other functional groups. "Deoxy" monosaccharides refer to monosaccharides having carbon atoms in the hexose backbone with only hydrogen substituents. Monosaccharides also include, but are not limited to, glucosamine (2-amino-2-deoxy-glucose; GlcN), N-acetylglucosamine (2-(acetylamino)-2-deoxy-glucose; GlcNAc), galactosamine (2-amino-2-deoxy-galactose; GalN;), N-acetylgalactosamine (2-(acetylamino)-2-deoxy-galactose; GalNAc), mannosamine (2-amino-2-deoxy-mannose; ManN), and N-acetylmannosamine (2-(acetylamino)-2-deoxy-mannose; ManNAc).

As used herein, the term "oligosaccharide" refers to a compound containing at least two sugars covalently linked together. Oligosaccharides include disaccharides, trisaccharides, tetrasaccharides, pentasaccharides, hexasaccharides, heptasaccharides, octasaccharides, and the like. Covalent linkages for linking sugars generally consist of glycosidic linkages (i.e., C—O—C bonds) formed from the hydroxyl groups of adjacent sugars. Linkages can occur between the 1-carbon (the anomeric carbon) and the 4-carbon of adjacent sugars (i.e., a 1-4 linkage), the 1-carbon (the anomeric carbon) and the 3-carbon of adjacent sugars (i.e., a 1-3 linkage), the 1-carbon (the anomeric carbon) and the 6-carbon of adjacent sugars (i.e., a 1-6 linkage), or the 1-carbon (the anomeric carbon) and the 2-carbon of adjacent sugars (i.e., a 1-2 linkage). A sugar can be linked within an oligosaccharide such that the anomeric carbon is in the α- or β-configuration. The oligosaccharides prepared according to the methods of the invention can also include linkages between carbon atoms other than the 1-, 2-, 3-, 4-, and 6-carbons.

As used herein, the term "α-linked" refers to a glycosidic bond wherein the reducing sugar is in the axial position with respect to the anomeric carbon of the non-reducing pyranose ring, as shown in formula A below. The term "β-linked" refers to a glycosidic bond wherein the reducing sugar (i.e., the sugar with a free hemiacetal at the anomeric carbon) is in the equatorial position with respect to the anomeric carbon of the non-reducing pyranose ring, as shown in formula B below. The carbon atoms in the formulas A and B are labeled 1, 2, 3, 4, 6, 1', 2', 3', 4', and 6' according to their positions in the backbones of the hexose subunits. One of skill in the art will appreciate that the α/β nomenclature and carbon numbering system applies to any disaccharide as well as to the particular isomers shown in formulas A and B.

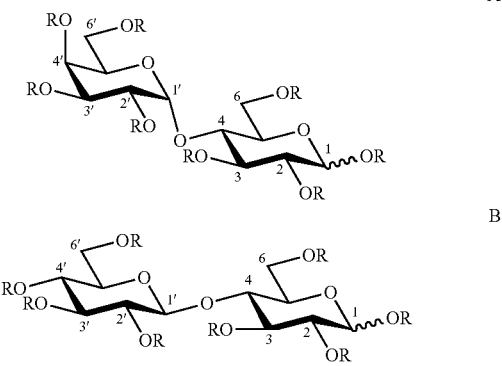

As used herein, the term "isomer" refers to a compound having the same bond structure as a reference compound but having a different three-dimensional arrangement of the bonds. An isomer can be, for example, an enantiomer or a diastereomer.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms such as, but not limited to, heptyl, octyl, nonyl, decyl, etc.

As used herein, the term "aryl" refers to an aromatic ring system having any suitable number of ring atoms and any suitable number of rings. Aryl groups can include any suitable number of ring atoms, such as 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl.

As used herein, the term "selectively-acylated" refers to a compound having two or more functional groups that can be converted to a —OC(O)alkyl moiety, but where at least one of the groups is converted to the —OC(O)alkyl moiety to a greater degree than all of the other functional groups.

As used herein, the term "forming a reaction mixture" refers to the process of bringing into contact at least two distinct species such that they mix together and can react, either modifying one of the initial reactants or forming a third distinct species, i.e., a product. It should be appreciated, however, the resulting reaction product can be produced directly from a reaction between the added reagents or from an intermediate from one or more of the added reagents which can be produced in the reaction mixture.

As used herein, the term "protected oligosaccharide" refers to an oligosaccharide wherein every hydroxyl group (or other ionizable moiety) is protected with a protecting group. A "protecting group" is a moiety that renders a functional group unreactive to a particular set of reaction conditions, but that is then removable in a later synthetic step so as to restore the functional group to its original state. Such protecting groups are well known to one of ordinary skill in the art, including those that are disclosed in *Protective Groups in Organic Synthesis,* 4th edition, T. W. Greene and P. G. M. Wuts, John Wiley & Sons, New York, 2006, which is incorporated herein by reference in its entirety.

As used herein, the term "silyl protecting group" refers to a protecting group represented by the formula —SiR$_3$, wherein each R is independently an alkyl group or aryl group as defined herein. Examples of silyl protecting groups include, but are not limited to, trimethylsilyl, triethylsilyl, and (tert-butyl)dimethylsilyl.

As used herein, the term "acylating agent" refers to a compound that is capable of reacting with a substrate compound to add a —C(O)alkyl moiety to the substrate. An acylating agent can be used, for example, to form an ester (i.e., RO—C(O)alkyl) on a substrate having a hydroxyl moiety (i.e., RO—H).

As used herein, the terms "hydroxyl" and "hydroxy" refer to a functional group represented by the formula —OH.

As used herein, the term "ketene" refers to a moiety represent by the formula R(C═C═O)R', wherein R and R' are independently substituted or unsubstituted hydrocarbon radicals.

As used herein, the term "carboxylic acid" refers to a moiety represented by the formula RC(O)OH, wherein R is a substituted or unsubstituted hydrocarbon radical.

As used herein, the term "acid chloride" refers to a moiety represented by the formula RC(O)Cl, wherein R is a substituted or unsubstituted hydrocarbon radical.

As used herein, the term "acid anhydride" refers to RC(O)—O—(O)CR', wherein R and R' are independently substituted or unsubstituted hydrocarbon radicals.

As used herein, the term "acid" refers to a substance that is capable of donating a proton (i.e., a hydrogen cation) to form a conjugate base of the acid. Examples of acids include, but are not limited to, acetic acid, formic acid, chloroacetic acid, bromoacetic acid, trichloroacetic acid, and benzoic acid.

As used herein, the term "base" refers to a substance that is capable of accepting a proton (i.e., a hydrogen cation) to form a conjugate acid of the base. Examples of bases include, but are not limited to, Huenig's base (i.e., diisopropylethylamine), lutidines including 2,6-lutidine (i.e., 2,6-dimethylpyridine), triethylamine, pyridine, lithium diisopropylamide, bis(trimethylsilyl)amides, and t-butoxides.

As used herein, the term "microwave radiation" refers to electromagnetic radiation having frequencies between about 300 MHz and about 300 GHz.

As used herein, the term "glycosyl iodide" refers to a saccharide compound having an iodide moiety replacing the hydroxyl group at the anomeric carbon at the reducing end of the saccharide.

As used herein, the term "glycosyl acceptor" refers to a compound RO—H that is capable of reacting with a saccharide or glycoside to form a compound having a formula RO—R', wherein R' is the saccharide and R is a substituted or unsubstituted hydrocarbon radical.

As used herein, the term "glycosyl donor" refers to a compound represented by the formula R'—X, wherein R' is a saccharide moiety and X is a suitable leaving group, that is capable of reacting with a glycosyl acceptor to form a compound having a formula RO—R', wherein R is a substituted or unsubstituted hydrocarbon radical.

As used herein, the term "elongated oligosaccharide" refers to an oligosaccharide compound having at least one more monosaccharide subunit than the parent saccharide from which it was derived. Alternatively, the term "elongated oligosaccharide" refers to an oligosaccharide having a non-carbohydrate moiety that was not present in the parent saccharide from which is was derived.

As used herein, the term "ceramide" encompasses all ceramides and sphingosines as conventionally defined. See, for example, Berg, et al. *Biochemistry,* 2002, 5th ed., W.H. Freeman and Co.

As used herein, the term "substituted glycerol" refers to a compound having a glycerol moiety substituted with one or two fatty acid moieties.

As used herein, the term "deprotected oligosaccharide" refers to an oligosaccharide having at least one hydroxyl moiety without a protecting group.

As used herein, the term "per-benzylated" or "per-O-benzylated" refers to a compound having one or more hydroxyl moieties wherein each hydroxyl moiety is protected as a benzyl ether: —O—CH$_2$Ph.

As used herein, the term "per-acetylated" or "per-O-acetylated" refers to a compound having one or more hydroxyl moieties wherein each hydroxyl moiety is protected as an acetyl group: —O—C(O)Me.

As used herein, the term "per-silylated" or "per-O-silylated" refers to a compound having one or more hydroxyl moieties wherein each hydroxyl moiety is protected as a silyl group: —O—Si(R)$_3$.

As used herein, the term "P$^k$ trisaccharide" refers to α-D-galactopyranosyl-(1→4)-β-D-galactopyranosyl-(1→4)-D-glucose and corresponding glycosides.

As used herein, the term "macrolide" refers to a compound characterized by a large (typically 14-to-16-membered) lactone ring having saccharide components within the ring, or substituted with pendant saccharides. Many macrolides demonstrate antibiotic and immunomodulatory activity.

III. Selectively-Acylated Disaccharides

In general, compounds of the present invention contain two monosaccharide subunits linked via a glycosidic bond. The glycosidic bond is an ether linkage (i.e., —O—) connecting the anomeric carbon of a first monosaccharide to any carbon of a second monosaccharide. Compounds of the present invention generally contain two hexose subunits, each hexose having six carbon atoms. Examples of monosaccharide subunits include, but are not limited to, derivatives of glucose, galactose, mannose, allose, altrose, gulose, idose, and talose. The monosaccharide can be a derivative of a deoxy sugar, such as fucose, 6-deoxyglucose, 2-deoxyglucose, 2-deoxygalactose, and the like.

Derivatives of a given monosaccharide have the same absolute stereochemical configuration as the parent monosaccharide with respect to the carbon backbone, but have one or more O-acyl or O-silyl moieties in place of one or more OH moieties. For example, compounds of Formula I can contain monosaccharide subunits that are derivatives of glucose (i.e., (2R,3R,4S,5S,6R)-6-(hydroxymethyl)tetrahydro-2H-pyran-2,3,4,5-tetraol), including, but not limited to, 6-acetylglucose (i.e., ((2R,3S,4S,5R,6R)-3,4,5,6-tetrahydroxytetrahydro-2H-pyran-2-yl)methyl acetate). The monosaccharide subunits can independently be a D sugar or an L sugar. Both monosaccharides can be D sugars, or both monosaccharides can be L sugars.

Accordingly, one aspect of the present invention provides a compound according to Formula I:

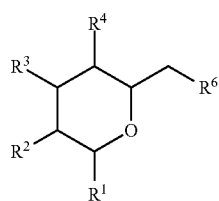

(I)

or an isomer thereof, wherein $R^1$, $R^2$, $R^3$, $R^4$, and $R^6$ can independently be hydrogen, —OR$^7$, an α-linked monosaccharide, or a β-linked monosaccharide. In compounds of the present invention, the monosaccharide has a structure according to Formula II.

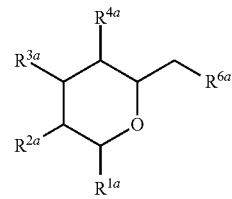

(II)

wherein $R^{1a}$, $R^{2a}$, $R^{3a}$, $R^{4a}$, and $R^{6a}$ can independently be hydrogen, —OR$^7$, or a linking moiety —O—, wherein the linking moiety links the monosaccharide to the moiety according to Formula I. Each $R^7$ can independently be hydrogen, —C(O)—C$_{1-6}$alkyl or —Si(R$^8$)$_3$, and each $R^8$ can independently be C$_{1-6}$ alkyl or C$_{6-10}$ aryl. In the compounds of the present invention, only one of $R^1$, $R^2$, $R^3$, $R^4$, and $R^6$ is the monosaccharide; at least one of $R^1$, $R^2$, $R^3$, $R^4$, and $R^6$ is —OR, wherein $R^7$ is —C(O)—C$_{1-6}$ alkyl; and at least one of $R^1$, $R^2$, $R^3$, $R^4$, $R^6$, $R^{1a}$, $R^{2a}$, $R^{3a}$, $R^{4a}$, and $R^{6a}$ is —OR$^7$, wherein $R^7$ is hydrogen or —Si(R$^8$)$_3$.

In some embodiments, the invention provides a compound of Formula I as described above wherein $R^1$, $R^2$, $R^3$, $R^4$, and $R^6$ can each independently be —OR$^7$, the α-linked monosaccharide, or the β-linked monosaccharide; $R^{1a}$, $R^{2a}$, $R^{3a}$, $R^{4a}$, and $R^{6a}$ can each independently be —OR$^7$ or the linking moiety —O—; each $R^7$ can independently be —C(O)—C$_{1-6}$alkyl or —Si(R$^8$)$_3$; and at least one of $R^1$, $R^2$, $R^3$, $R^4$, $R^6$, $R^{1a}$, $R^{2a}$, $R^{3a}$, $R^{4a}$, and $R^{6a}$ is —OR$^7$, wherein $R^7$ is —Si(R$^8$)$_3$.

The monosaccharide subunits in the compounds of the invention can be linked to each other in a number of configurations. The monosaccharides can be linked, for example, via a 1-4 linkage, wherein the anomeric carbon of the first monosaccharide is linked to the 4 carbon of the second monosaccharide via an ether bond. The monosaccharides can be linked via a 1→1 linkage, a 1→2 linkage, a 1-3 linkage, or a 1-6 linkage. In some embodiments, the monosaccharide subunits are linked together via a 1→4 linkage, a 1→6 linkage, or a 1→1 linkage. The compounds of the invention can contain other linkages, depending on the structures of the monosaccharide subunits. Any linkage can be an α linkage, wherein the —O— moiety is axial with respect to the anomeric carbon, or a p linkage, wherein the —O— moiety is equatorial with respect to the anomeric carbon.

In some embodiments, $R^1$ is selected from the α-linked monosaccharide and the 3-linked monosaccharide. In some embodiments, one of $R^{1a}$, $R^{4a}$ and $R^{6a}$ is the linking moiety —O—.

The compounds of the invention can be substituted with —C(O)—C$_{1-6}$alkyl moieties in various positions. The compounds of the invention can have 1, 2, 3, 4, 5, 6, or 7 —C(O)—C$_{1-6}$alkyl moieties in various positions. In some embodiments, for example, the compounds can have 1 —C(O)—C$_{1-6}$alkyl moiety at the 6' position. In some embodiments, the compounds can have 2 —C(O)—C$_{1-6}$alkyl moieties at the 6 and 6' positions. In some embodiments, the compounds can have 2 —C(O)—C$_{1-6}$alkyl moieties at the 1 and 6' positions. In some embodiments, the compounds can have 3 —C(O)—C$_{1-6}$ alkyl moieties at the 1, 6, and 6' positions. In some embodiments, the compounds can have 4 —C(O)—C$_{1-6}$ alkyl moieties at the 1, 2, 6, and 6' positions. In some embodiments, the compounds can have 5 —C(O)—$C_{1-6}$ alkyl moieties at the 1, 2, 3, 4, and 6' positions. In some embodiments, the compounds can have 6 —C(O)—$C_{1-6}$ alkyl moieties at the 1, 2, 3, 4, 2', and 6' positions. In some embodiments, the compounds can have 6 —C(O)—$C_{1-6}$ alkyl moieties at the 2, 3, 4, 6, 4', and 6' positions. In some embodiments, the compounds can have 7 —C(O)—$C_{1-6}$ alkyl moieties at the 1, 2, 3, 4, 2', 3', and 6' positions. In some embodiments, the compounds can have 7 —C(O)—$C_{1-6}$ alkyl moieties at the 1, 2, 3, 6, 2', 3', and 6' positions. In some embodiments, the compounds of the invention can have other substitution patterns, depending on the structures of the monosaccharide subunits.

In some embodiments, $R^6$ can be —$OR^7$, wherein $R^7$ can be —C(O)—$C_{1-6}$ alkyl. In some embodiments, at least one of $R^{1a}$, $R^{2a}$, $R^{3a}$, $R^{4a}$, and $R^{6a}$ can be —$OR^7$, wherein $R^7$ can be —C(O)—$C_{1-6}$alkyl.

Compounds of Formula I constitute useful derivatives of biologically and synthetically important disaccharides. The disaccharide derivatives have the same stereochemical configuration as the parent disaccharides with respect to the carbon backbone, but have one or more O-acyl or O-silyl moieties in place of one or more OH moieties. Compounds of Formula I include, but are not limited to, derivatives of lactose, melibiose, trehalose, cellobiose, maltose, sophorose, laminaribiose, gentiobiose, mannobiose, rutinose, and the like.

In some embodiments, the compound of Formula I has the structure

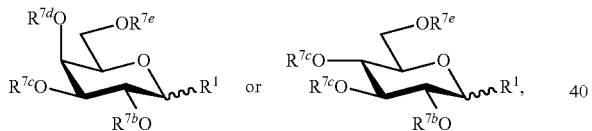

wherein $R^{7b}$, $R^{7c}$, $R^{7d}$, and $R^{7e}$ are each independently —C(O)—$C_{1-6}$ alkyl or —$Si(R^8)_3$.

In some embodiments, the compound has a structure selected from

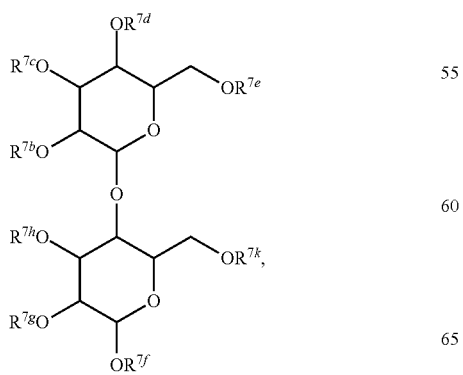

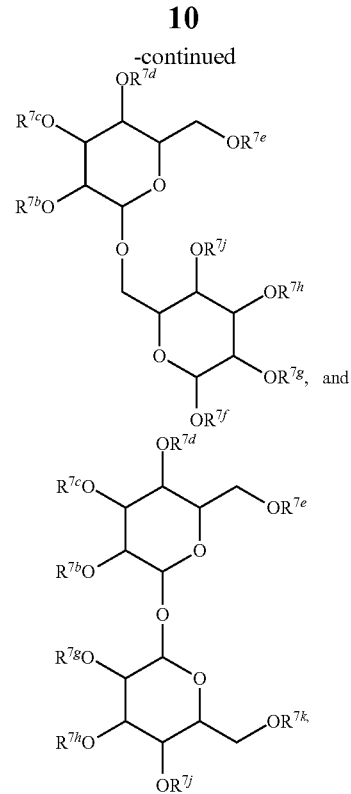

wherein $R^{7b}$, $R^{7c}$, $R^{7d}$, $R^{7e}$, $R^{7f}$, $R^{7g}$, $R^{7h}$, $R^{7j}$, and $R^{7k}$ are each independently —C(O)—$C_{1-6}$ alkyl or —$Si(R^8)_3$.

In some embodiments, the compound has the structure

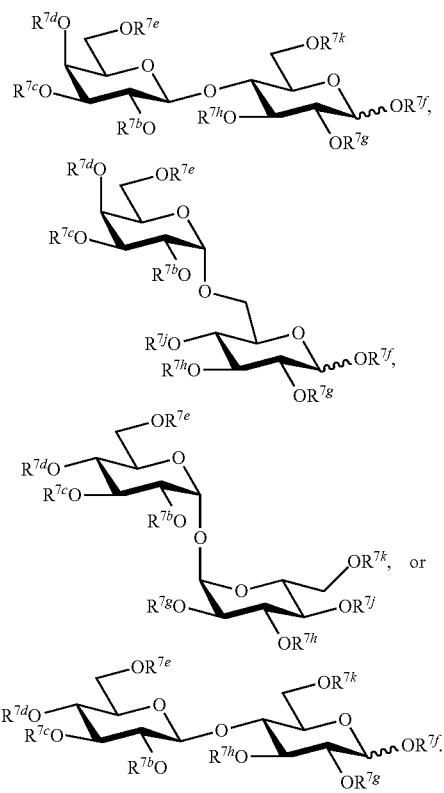

In some embodiments, $R^{7e}$ can be —C(O)—$C_{1-6}$ alkyl. In some embodiments, at least one of $R^{7b}$, $R^{7c}$, $R^{7d}$, $R^{7f}$, $R^{7g}$, $R^{7h}$, $R^{7j}$, and $R^{7k}$ can be —C(O)—$C_{1-6}$ alkyl.
In some embodiments, the compound can be:
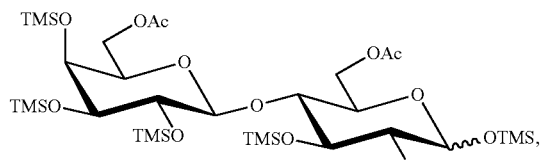
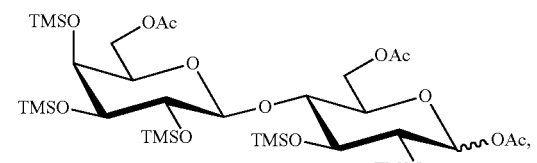
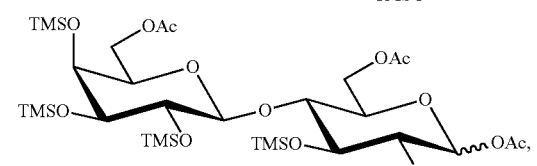
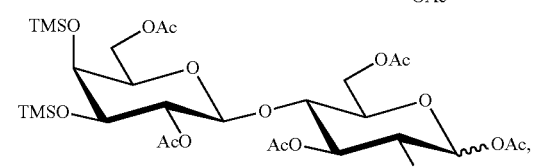
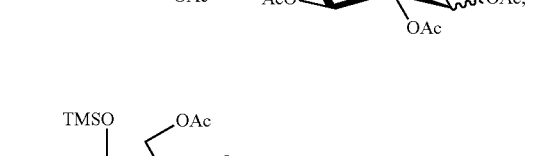
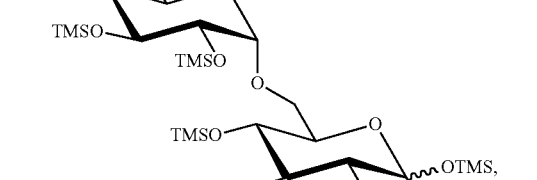
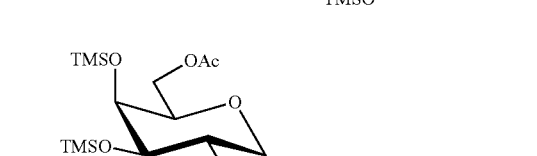
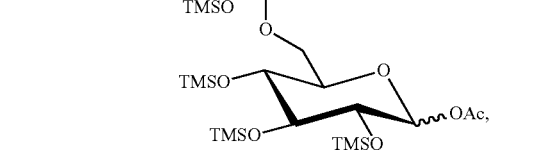
-continued
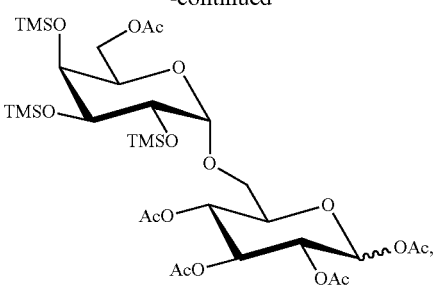
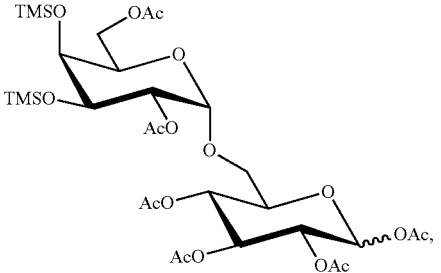
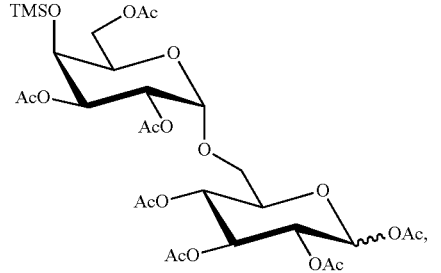
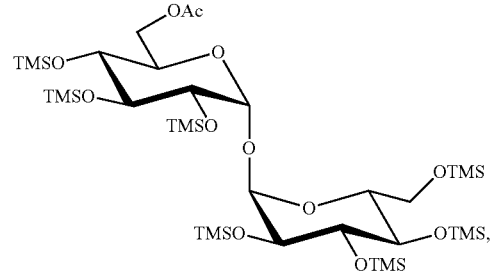
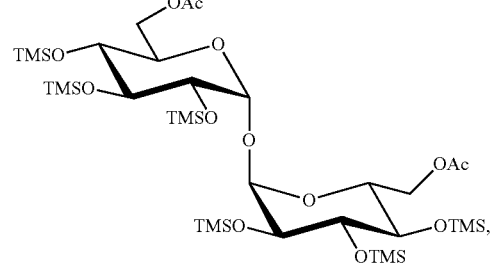
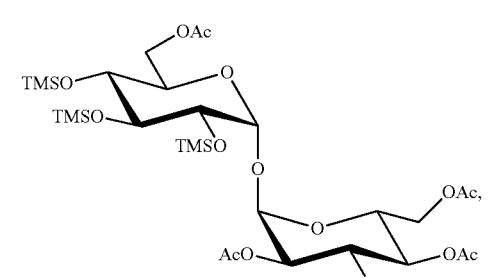

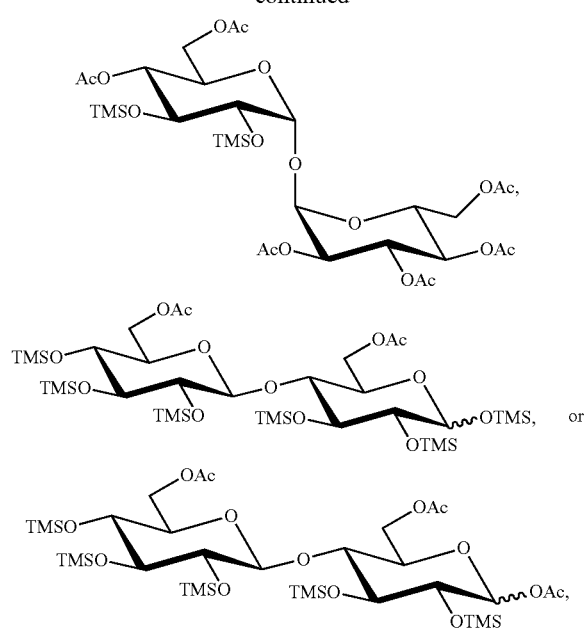
wherein each TMS is —Si(Me)$_3$ and each Ac is —C(O)Me.
In some embodiments, the compound can be:
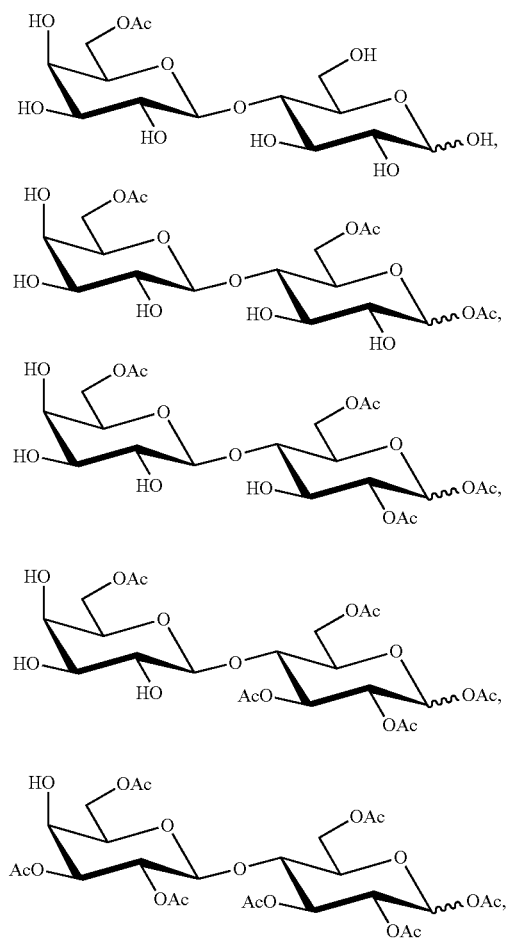
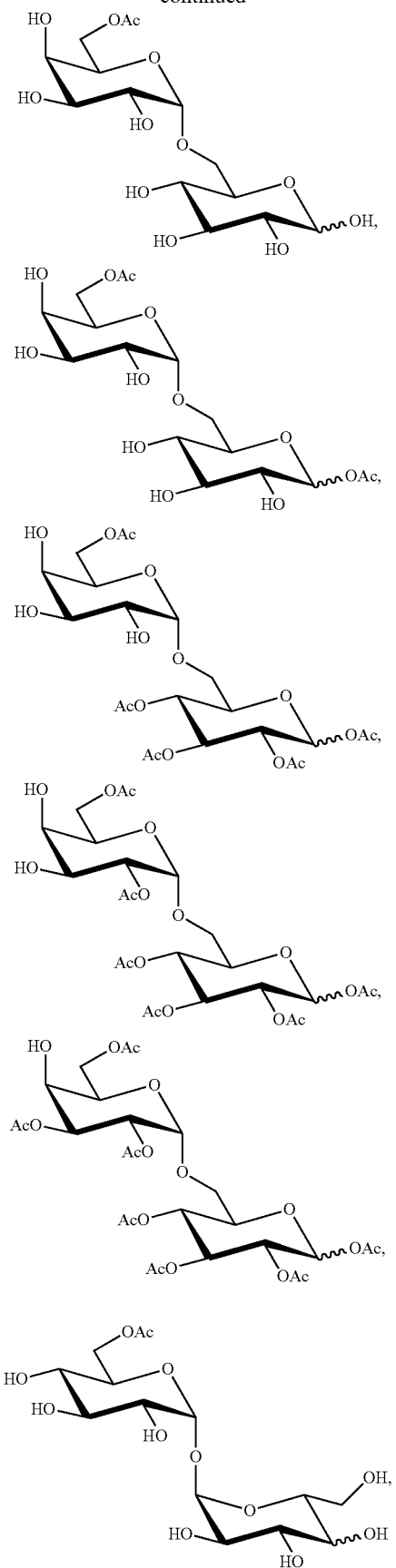

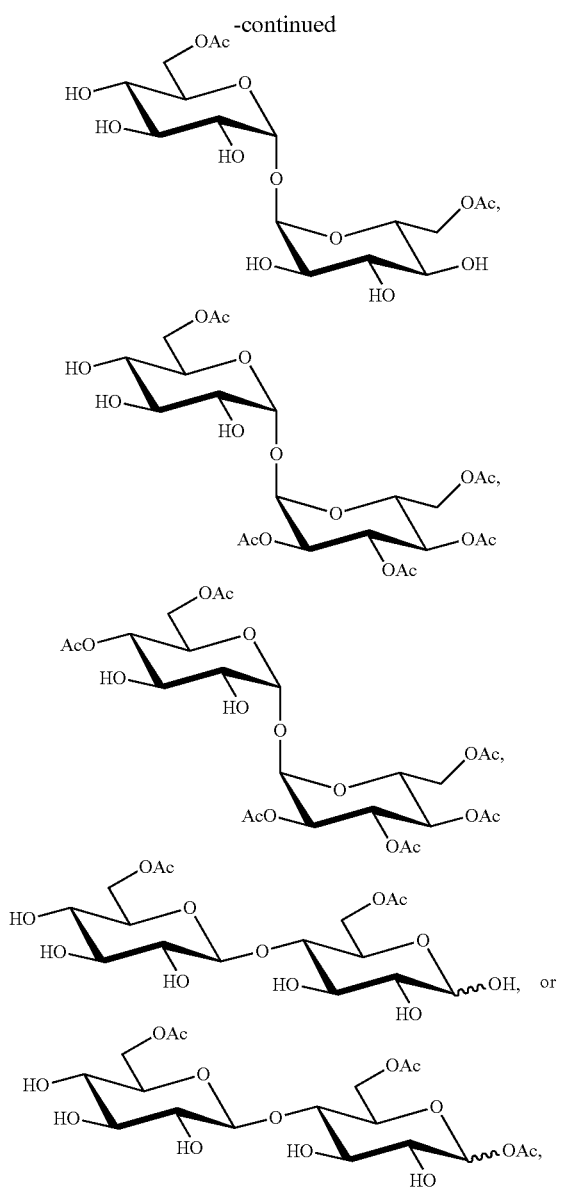

wherein each Ac is —C(O)Me.

IV. Methods for Preparing Selectively Acylated Oligosaccharides

In a related aspect, the invention provides a method for preparing a selectively-acylated oligosaccharide. The method includes forming a reaction mixture containing a protected oligosaccharide and an acylating agent, wherein the protected oligosaccharide includes at least three hydroxyl moieties and each hydroxyl moiety is protected with a silyl protecting group. The reaction mixture is formed under conditions sufficient to selectively replace at least one silyl protecting group with a —C(O)—$C_{1-6}$alkyl group, and the selectively-acylated oligosaccharide includes at least one —C(O)—$C_{1-6}$ alkyl group and at least one silyl protecting group.

Any suitable protected oligosaccharide can be used in the methods of the invention. In general, suitable protected oligosaccharides contain at least two per-silylated monosaccharide subunits. As defined above, a "per-silylated" monosaccharide refers to a monosaccharide having the same absolute stereochemical configuration as the parent monosaccharide with respect to the carbon backbone, but having an O-silyl moiety in place of each —OH moiety. Examples of protected oligosaccharide include, but are not limited to, compounds of formula C, having $R^8$ groups as described above. For example, the protected oligosaccharide can contain two or more per-silylated glucose subunits, including, but not limited to, per-O-trimethylsilyl glucose. The protected oligosaccharides can contain more than two per-silylated monosaccharide subunits. In some embodiments, the protected oligosaccharide is a per-silylated disaccharide.

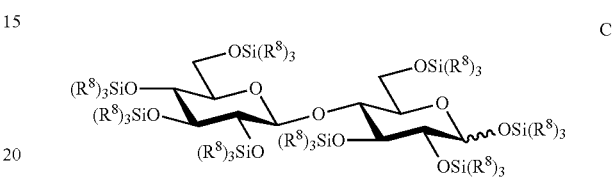

In some embodiments, the protected oligosaccharide includes two or more protected monosaccharide units which are covalently linked together via an α-(1→1) linkage, a β-(1→1) linkage, an α-(1→4) linkage, a β-(1→4) linkage, an α-(1→6) linkage, or a β-(1→6) linkage.

The methods of the invention can be used to prepare any of the disaccharide compounds described above. In some embodiments, the selectively-acylated oligosaccharide is a compound according to Formula I:

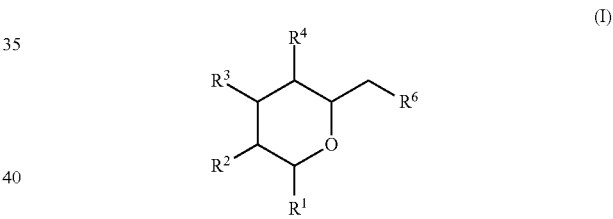

or an isomer thereof, wherein $R^1$, $R^2$, $R^3$, $R^4$, and $R^6$ can each independently be hydrogen, —$OR^7$, an α-linked protected monosaccharide, or a β-linked protected monosaccharide. The protected monosaccharide has the structure according to Formula II:

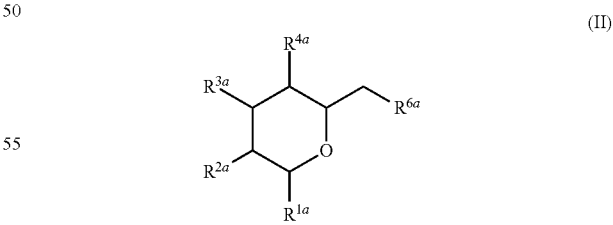

wherein $R^{1a}$, $R^{2a}$, $R^{3a}$, $R^{4a}$, and $R^{6a}$ can each independently be —$OR^7$ or a linking moiety —O—, wherein the linking moiety links the monosaccharide to the moiety according to Formula I. For these selectively-acylated oligosaccharides, each $R^7$ can independently be —C(O)—$C_{1-6}$ alkyl or —Si$(R^8)_3$; and each $R^8$ can independently be $C_{1-6}$ alkyl or $C_{6-10}$ aryl. For these selectively-acylated oligosaccharides, only one of $R^1$, $R^2$, $R^3$, $R^4$, and $R^6$ is the protected monosaccharide; at least one of $R^1$, $R^2$, $R^3$, $R^4$, $R^6$, $R^{1a}$, $R^{2a}$, $R^{3a}$, $R^{4a}$, and $R^{6a}$ is —$OR^7$ where $R^7$ is —C(O)—$C_{1-6}$ alkyl; and at least one of $R^1$, $R^2$, $R^3$, $R^4$, $R^6$, $R^{1a}$, $R^{2a}$, $R^{3a}$, $R^{4a}$, and $R^{6a}$ is —$OR^7$ where $R^7$ is —Si($R^8$)$_3$.

In some embodiments, the selectively-acylated oligosaccharide has the structure:

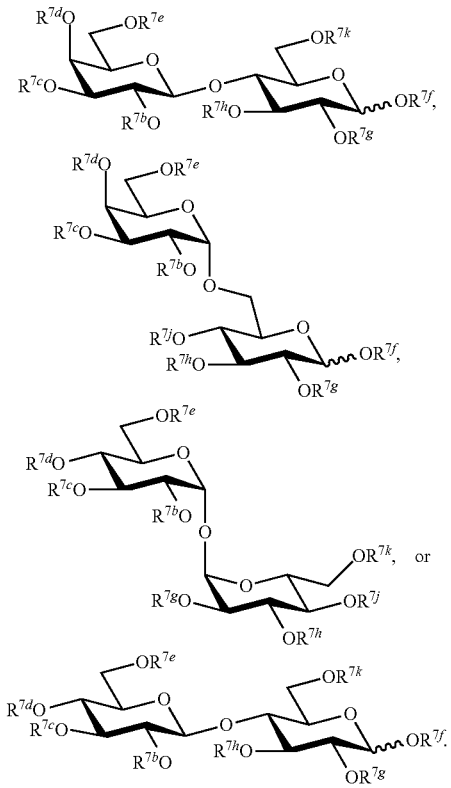

wherein $R^{7b}$, $R^{7c}$, $R^{7d}$, $R^{7e}$, $R^{7f}$, $R^{7g}$, $R^{7h}$, $R^{7j}$, and $R^{7k}$ can each independently be —C(O)—$C_{1-6}$ alkyl or —Si($R^8$)$_3$. In some embodiments, $R^{7e}$ is —C(O)—$C_{1-6}$ alkyl and at least one of $R^{7b}$, $R^{7c}$, $R^{7d}$, $R^{7f}$, $R^{7g}$, $R^{7h}$, $R^{7j}$, and $R^{7k}$ is —C(O)—$C_{1-6}$ alkyl.

Any suitable acylating agent can be used in the methods of the invention. Examples of useful acylating agents include, but are not limited to, carboxylic acids, acid chlorides, acid anhydrides, ketenes, activated esters such as pentafluorophenyl esters and N-hydroxysuccinimidyl esters, and carbonylimidazoles. Acylating agents can be used in conjunction with catalysts and coupling reagents such as carbodiimides (e.g., dicyclohexylcarbodiimide and N-(3-dimethylaminopropyl)-N'-ethylcarbodiimide), nucleophilic catalysts (e.g., N,N-dimethylaminopyridine), Lewis acids (e.g., copper (II) triflate), benzotriazoles, phosphonium reagents, uranium reagents, and formamidinium reagents. In some embodiments, the acylating agent is selected from a ketene, a carboxylic acid, an acid chloride, and an acid anhydride. In some embodiments, the acylating agent is acetic anhydride.

The reaction mixture generally includes a suitable organic acid. Examples of suitable acids include acetic acid, formic acid, chloroacetic acid, bromoacetic acid, trichloroacetic acid, and benzoic acid. Other acids can also be suitable in the methods of the invention. Combinations of two or more acids can be used. The reaction mixture can include any suitable amount of acid. In general, the reaction mixture contains from about 1 to about 10 equivalents of acid with respect to the protected oligosaccharide. In some embodiments, the reaction mixture contains from about 1 to about 7 equivalents of acid with respect to the protected oligosaccharide.

In some embodiments, the invention provides methods for forming a selectively-acylated oligosaccharide as described above wherein the reaction mixture further includes an acid that can be acetic acid, formic acid, or trichloroacetic acid. In some embodiments, the acid is acetic acid.

The reaction mixture generally includes a suitable base. Examples of suitable bases include Huenig's base (i.e., diisopropylethylamine), lutidines including 2,6-lutidine (i.e., 2,6-dimethylpyridine), triethylamine, tributylamine, pyridine, 1,8-diazabicycloundec-7-ene (DBU), 1,5,7-triazabicyclo(4.4.0)dec-5-ene (TBD), 1,5-diazabicyclo[4.3.0] non-5-ene (DBN), 1,1,3,3-tetramethylguanidine (TMG), 2,2,6,6-tetramethylpiperidine (TMP), quinuclidine, and the collidines. Other bases can also be suitable in the methods of the invention. Combinations of two or more bases can be used. The reaction mixture can include any suitable amount of base. In general, the reaction mixture contains from about 1 to about 50 equivalents of base with respect to the protected oligosaccharide. In some embodiments, the reaction mixture contains from about 15 to about 25 equivalents of base with respect to the protected oligosaccharide.

In some embodiments, the invention provides methods for forming a selectively-acylated oligosaccharide as described above wherein the reaction mixture further includes at least one base that can be pyridine, diisopropylethylamine, triethylamine, or 1,8-diazabicycloundec-7-ene. In some embodiments, the reaction mixture includes at least two bases that can be pyridine, diisopropylethylamine, triethylamine, or 1,8-diazabicycloundec-7-ene.

Conditions for preparing the selectively acylated oligosaccharides of the present invention can proceed using a variety of other solvents and reagents. Solvents useful for the preparation of the selectively acylated oligosaccharides of the present invention include, but are not limited to, N-methyl pyrrolidinone (NMP), dimethylformamide (DMF), methylene chloride, chloroform, benzene, toluene, acetonitrile, tetrahydrofuran (THF), ether, dioxane, glyme, diglyme, ethyl acetate, methanol, ethanol and isopropanol. One of skill in the art will appreciate that other solvents and solvent combinations are useful in the present invention.

The preparation of the selectively acylated oligosaccharides can proceed at a variety of temperatures and times. In general, preparation of the selectively acylated oligosaccharides can be achieved using reaction times of several minutes to several days. For example, reaction times of from about 12 hours to about 7 days can be used. In some embodiments, reaction times of 1-5 days can be used. In some embodiments, reaction times of from about 10 minutes to about 10 hours can be used. In general, preparation of the selectively acylated oligosaccharides can be achieved at a temperature of from about 0° C. to about 200° C. For example, reactions can be conducted at 15-100° C. In some embodiments, reactions can be conducted at 20-80° C. In some embodiments, reactions can be conducted at 100-150 OC.

In some embodiments, reaction times of from about 12 hours to about 7 days can be used at 15-100° C. In some embodiments, reaction times of 1-5 days at 20-80° C. can be used. In some embodiments, reaction times of from about 10 minutes to about 10 hours at temperatures of from about 100° C. to about 150° C. are used. One of skill in the art will appreciate that the time, temperature and solvent are dependent on each other, and changing one can require changing the others to prepare the selectively acylated oligosaccharides of the present invention.

In some embodiments, the reaction mixture is formed at a temperature of from about 4° C. to about 200° C. In some embodiments, the reaction mixture is formed at a temperature of from about 100° C. to about 200° C.

In some embodiments, the method further includes exposing the reaction mixture to microwave radiation. Microwave irradiation can be performed at any appropriate time, temperature or power setting. Reactions can be conducted, for example, at temperature of from about 50° C. to about 150° C., or at a temperature of up to about 200° C. Reactions can be conducted for anywhere from a few minutes to several hours. Reactions can be conducted, for example, for less than 30 minutes, less than 1 hour, less than 5 hours, or less than 10 hours. When using microwave irradiation, the preparation of the selectively acylated oligosaccharide can be achieved in less than 10 hours at up to 200 OC. In some embodiments, the selectively acylated oligosaccharide can be prepared in less than 5 hours at from 50 to 150° C. The microwave can operate at a variety of power settings, up to about 1000 Watts. In some embodiments, the microwave operates at less than 500 Watts. One of skill in the art will appreciate that other temperatures, times, and microwave power settings are useful in the present invention.

In some embodiments, the method further includes converting the selectively acylated oligosaccharide to a glycosyl iodide. The glycosyl iodide can be prepared, for example, by methods described in U.S. patent application Ser. No. 12/595,214 (issued as U.S. Pat. No. 8,624,006) the entirety of which is incorporated herein by reference. In general, preparation of a glycosyl iodide includes contacting a selectively acylated oligosaccharide with an iodine source such as trimethylsilyl iodide (TMSI), sodium iodide, potassium iodide, and N-iodosuccinimide. The selectively acylated oligosaccharide and the iodine source are contacted under conditions sufficient to replace one of the O-acyl or O-silyl moieties of the oligosaccharides with an iodide moiety (i.e., "—I").

In some embodiments, the method further includes contacting the glycosyl iodide with a glycosyl acceptor to form an elongated oligosaccharide. An "elongated oligosaccharide" contains the glycosyl iodide glycone moiety which is covalently linked to one or more additional monosaccharide subunits, or to a suitable non-carbohydrate moiety. The non-carbohydrate moiety can be, for example, a lipid, a peptide, a protein, a fluorophore, a chromophore, or a radiolabel.

The methods of the invention can be used to prepare a number of useful glycolipids. The glycolipids can be prepared by contacting the glycosyl iodide with a lipid glycosyl acceptor. Any lipid is useful in the methods of the present invention. Exemplary lipids include ceramides and substituted glycerols. When the lipid is a ceramide, the ceramide includes a fatty acid component and either a sphingosine or a phytosphingosine. In some embodiments, the lipid is a ceramide or a substituted glycerol. In other embodiments, the lipid is a ceramide. In some other embodiments, the ceramide is a sphingosine. In still other embodiments, the ceramide is a phytosphingosine. In yet other embodiments, the substituted glycerol is substituted with 1 or 2 fatty acids.

The fatty acids useful in the present invention include, but are not limited to, butyric acid (C4), caproic acid (C6), caprylic acid (C8), capric acid (C10), lauric acid (C12), myristic acid (C14), palmitic acid (C16), palmitoleic acid (C16), stearic acid (C18), oleic acid (C18), vaccenic acid (C18), linoleic acid (C18), alpha-linoleic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). The fatty acids useful in the present invention have at least four carbon atoms in the chain. The fatty acids of the present invention can have between 10 and 26 atoms in the chain. The fatty acids can have between 14 and 22 atoms in the chain, or between 16 and 20 atoms in the chain. The fatty acids can have 26 atoms in the chain. The fatty acids of the present invention can be saturated, mono-unsaturated, or poly-unsaturated. One of skill in the art will recognize that other fatty acids are useful in the present invention.

Substituted glycerols useful in the method of the present invention include glycerol substituted with fatty acids as described above. In some cases, the glycerol is substituted with 1 or 2 fatty acids, so that the remaining hydroxy group of glycerol can react with the α-iodo sugar.

In some embodiments, the lipid is a sphingosine derivative or phytosphingosine derivative such as:

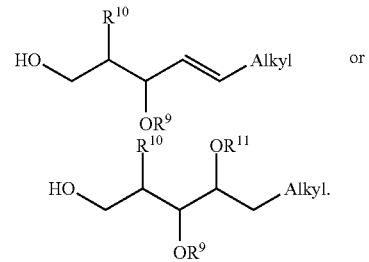

$R^9$ and $R^{11}$ of the formula are independently H or a protecting group, such as those described above. $R^{10}$ is an amine, an amide or an azide. In some embodiments, $R^9$ is a para-methoxybenzyl group. In other embodiments, $R^9$ is a tri-methyl silyl, tri-ethyl silyl, tri-isopropyl silyl, or tertbutyl-dimethyl-silyl groups. "Alkyl" is any $C_{1-20}$ alkyl that can be branched or unbranched, saturated or partially unsaturated, and optionally substituted with hydroxy, alkoxy, aldehyde, ester or carboxy groups.

In some other embodiments, the lipid can be

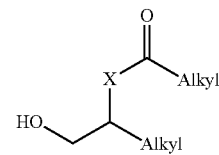

wherein X is O or NH, and alkyl is as defined above.

In some embodiments, the method further includes contacting the glycosyl iodide with a glycosyl acceptor as described above, wherein the glycosyl acceptor includes a ceramide or a substituted glycerol. Such glycosylation reactions are described in U.S. Pat. No. 8,624,006. The glycosylation reaction can be conducted with one or more additional reagents that promote the transfer of the glycosyl iodide glycone moiety to the glycosyl acceptor. Such agents include, but are not limited to, Lewis acids (such as aluminum chloride, iron (III) chloride, silver triflate, and the like) and quaternary ammonium iodide salts (such as tetramethylammonium iodide, tetrabutylammonium iodide, and the like). One of skill in the art will appreciate that other reagents can be used to promote the transfer of the glycosyl iodide glycone moiety to the glycosyl acceptor.

The selectively acylated oligosaccharides can also serve as precursors for glycosyl acceptors that can be further elaborated to provide elongated oligosaccharides. In general, a selectively acylated oligosaccharide is converted to a deprotected oligosaccharide by removing one or more O-silyl moieties. The deprotected oligosaccharide can then be used as a glycosyl acceptor in glycosylation reactions such as those described above. As such, some embodiments of the invention provide methods for preparing selectively-acylated oligosaccharides as described above, wherein the method further includes removing at least one protecting group from the selectively acylated oligosaccharide to form a deprotected oligosaccharide.

Any suitable method for removing one or more O-silyl moieties from the selectively acylated oligosaccharide can be used in the methods of the invention. A number of methods for removal of O-silyl moieties are known in the art, as detailed in *Protective Groups in Organic Chemistry, Peter G. M. Wuts and Theodora W. Greene*, 4th Ed., 2006. Useful reagents for removal of O-silyl moieties include, but are not limited to, acidic resins (such as Dowex resins, Rexyn resins, and the like), fluoride reagents (such as tetrabutylammonium fluoride and the like), oxidizing agents (such as 2,3-dichloro-5,6-dicyano-p-benzoquinone and the like), reducing agents (such as bis(2-methoxyethoxy)aluminumhydride and the like), and Lewis acids (such as iron (III) chloride, boron trifluoride, and the like). One of skill in the art will appreciate that other reagents will be useful for removal of O-silyl moieties, depending on the structure of the particular silyl protecting group.

The methods of the invention can be used to convert the deprotected oligosaccharides described above to a number of biologically and synthetically important elongated oligosaccharides. The elongated oligosaccharides can be tumor associated carbohydrate antigens (TACAs), which are known to exist on the surface of malignant cancer cells at elevated levels. One class of TACAs, for example, is the "globo" series of oligosaccharides including Gb3 (α-D-galactopyranosyl-(1→4)-β-D-galactopyranosyl-(1→4)-D-glucose, also known as the "$P^k$" trisaccharide). Other non-limiting examples of TACAs include, Gb5, Gb4, globo-H, Bb4, Bb3, B19, chitotriose, chitotetraose, cellotriose, sialyl-Lewis$^x$ (SLe$^x$), sialyl-Lewis$^a$ (SLe$^a$), GM1, fucosyl-GM1, GM2, GM3, fucosyl-GM3, DSGG, GD2, and GD3. One of skill in the art will appreciate that the methods of the invention can be used to prepare other useful oligosaccharides.

In order to form a TACA or another elongated oligosaccharide, the deprotected oligosaccharide is contacted with a suitable glycosyl donor. Suitable glycosyl donors include, but are not limited to, glycosyl iodides, glycosyl bromides, glycosyl trichloroacetimidates, and thioglucosides. Reactive groups in the glycosyl donor can be protected with various suitable protecting groups, as is well known in the art. Accordingly, some embodiments of the invention provide methods for preparing selectively-acylated oligosaccharides including forming a deprotected oligosaccharide as described above, and further including contacting the deprotected oligosaccharide with a glycosyl donor to form an elongated oligosaccharide. In some embodiments, the glycosyl donor includes a per-benzylated glycosyl iodide. In some embodiments, the elongated oligosaccharide comprises a $P^k$ trisaccharide moiety.

Deprotected oligosaccharides can also be used to prepare other useful compounds, by reacting deprotected hydroxyl moieties with non-carbohydrate compounds. As a non-limiting example, deprotected oligosaccharides can be used to prepare lipid derivatives with surfactant properties such as sophorolipids, succinoyl trehalose lipids, and dirhamnolipids. Sophorolipids contain a sophorose moiety that is linked to 17-hydroxyoleic acid via a glycosidic bond; intramolecular lactone formation between the sophorose 4' hydroxyl group and the hydroxyoleic carboxylate results in a macrolide structure. Related macrolides have lactones formed from various long-chain hydroxy acids and oligosaccharides including, melibiose, lactose, and others. As such, some embodiments of the invention provide methods for preparing selectively-acylated oligosaccharides including forming a deprotected oligosaccharide as described above, and further including converting the deprotected oligosaccharide to a macrolide.

V. Examples

General

Proton nuclear magnetic resonances ($^1$H NMR), carbon nuclear magnetic resonances ($^{13}$C NMR), and 2 dimensional NMR spectra were recorded in deuterated solvents on Varian (600 MHz) and Bruker Avance600 (600 MHz) and Avance800 (800 MHz) spectrometers. Chemical shifts are reported in parts per million (ppm, δ) relative to the residual protonated solvent (CDCl$_3$, δ 7.26; CD$_3$OD, δ 3.31). $^1$H NMR splitting patterns are designated as singlet (s), doublet (d), doublet of doublets (dd) or apparent triplet (app. t). Splitting patterns that could not be visualized or easily interpreted were designated as broad (br) or multiplet (m). Coupling constants are reported in Hertz (Hz). Analytical thin layer chromatography (TLC) was carried out on Glass-backed TLC plates (Silica Gel 60 with a 254 nm fluorescent indicator, 250 mm layer thickness) that were used without further manipulation and stored over desiccant. TLC plates were visualized by heating plates that were dipped in a solution of ammonium molybdate/cerium (IV) sulfate stain. Flash column chromatography was performed on Dynamic Adsorbents Inc. silica gel (32-63 u). Solvent mixtures used for TLC and flash column chromatography are reported in v/v ratios. The unprotected disaccharides were dried in a vacuum oven at 80° C. for 24 hours. All other commercially available reagents and solvents used without further purification, and all reactions were carried out in oven-dried glassware.

Typical Procedure for Regioselective Silyl Exchange of Per-O-TMS Disaccharides.

In a 10 mL microwave reactor vessel or 25 mL round bottom flask, per-O-TMS disaccharide (lactose, melibiose or trehalose) (500 mg, 0.54 mmol or 230 mg, 0.25 mmol) was dissolved in anhydrous benzene (3 mL). The solvent was removed under rotary evaporation with argon backfilling. The azeotropic distillation was repeated two additional times to dryness affording viscous syrup. To the reaction flask was added a dry stirring bar, anhydrous pyridine (2.0 mL/per mmol TMS sugar), acetic anhydride (1.5 mL/per mmol TMS sugar), and glacial acetic acid (2-8 equiv.). The reaction vessel was either placed under room temperature or was heated by conventional oil bath or was subjected to microwave irradiation (standard mode, 100 W, 125° C. or 110° C., ~40 psi) for various time intervals. Once TLC showed the reaction was complete, the reaction mixture was transferred into a 50 mL round bottom flask where it was azeotroped with copious amounts of anhydrous benzene to dryness. The crude foam was immediately purified by flash column chromatography (hexanes/ethyl acetate/5% triethylamine) to afford the partially acetylated products.

Example 1

Regioselective Acylation of Per-O-Silylated Lactose

Per-O-silylated lactose was prepared via known methods and selectively acylated using a mixture of anhydrous pyridine and acetic anhydride using 3 equivalents of glacial acetic acid (Table 1, Entry 1). After 5 days, the product mixture was purified using flash column chromatography affording the 6,6'-di-O-acetyl-lactoside (1), the 1,6,6'-tri-O-acetyl-lactoside (2), and the 1,2,6,6'-tetra-O-acetyl-lactoside (3). Table 1 includes the first examples of silyl exchange on a disaccharide where the anomeric hydroxyl group is also silylated. This advancement significantly reduces the number of steps required to transform the disaccharide into a donor.

It is noteworthy that 3 was only isolated from the reaction at room temperature and not from any reactions in which the mixture was heated. By increasing the reaction temperature from rt to 40° C. and 60° C., similar product mixtures were obtained, however the reaction time decreased from 5 d to 60 h and 36 h, respectively (Table 1, Entries 2 and 3).

Initially, only a small amount of 4'-O-TMS-hepta-O-acetyl-lactoside (4) was isolated as confirmed by NMR analysis. Heating to 80° C. reduced the reaction time to 1 d while increasing the yield of 4, a molecule of significant interest as a precursor to $P^k$ trisaccharide, from 5% to 23%.

Microwave assistance afforded a similar distribution of compounds 1 and 2 after 75 minutes as obtained after 5 d at rt; but compounds 3 and 4 were not observed (Table 1, Entry 5). Increasing the acetic acid equivalents to greater than five resulted in the exclusive formation of compounds 4 and 5, (Table 1, Entries 6 and 7). Thus, the orthogonally protected species 4 was prepared in 2 steps from commercially available D-lactose and in just under 4 h from per-O-TMS lactose. This is the first reported synthesis of compounds 1-4. Moreover, per-O-TMS lactose could be regenerated by deacetylation of 5 and re-silylation in 92% yield.

TABLE 1

Selective acetylation of per-O-TMS lactose.

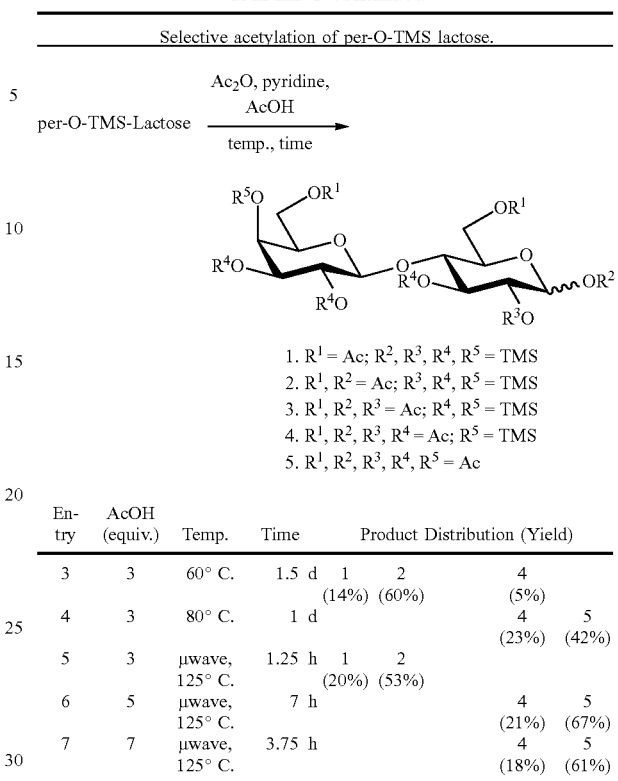

1. $R^1$ = Ac; $R^2$, $R^3$, $R^4$, $R^5$ = TMS
2. $R^1$, $R^2$ = Ac; $R^3$, $R^4$, $R^5$ = TMS
3. $R^1$, $R^2$, $R^3$ = Ac; $R^4$, $R^5$ = TMS
4. $R^1$, $R^2$, $R^3$, $R^4$ = Ac; $R^5$ = TMS
5. $R^1$, $R^2$, $R^3$, $R^4$, $R^5$ = Ac

| Entry | AcOH (equiv.) | Temp. | Time | Product Distribution (Yield) | | | |
|---|---|---|---|---|---|---|---|
| 1 | 3 | rt | 5 d | 1 (19%) | 2 (55%) | 3 (12%) | |
| 2 | 3 | 40° C. | 2.5 d | 1 (6%) | 2 (63%) | | |
| 3 | 3 | 60° C. | 1.5 d | 1 (14%) | 2 (60%) | | 4 (5%) |
| 4 | 3 | 80° C. | 1 d | | | | 4 (23%) / 5 (42%) |
| 5 | 3 | μwave, 125° C. | 1.25 h | 1 (20%) | 2 (53%) | | |
| 6 | 5 | μwave, 125° C. | 7 h | | | | 4 (21%) / 5 (67%) |
| 7 | 7 | μwave, 125° C. | 3.75 h | | | | 4 (18%) / 5 (61%) |

Example 1.1

(6-O-Acetyl-2,3,4-tri-O-trimethylsilyl-β-D-galactopyranosyl)-(1-4)-O-(6-O-acetyl-1,2,3-tri-O-trimethylsilyl)-D-glucopyranoside (1)

Following the general procedure described above, per-O-TMS lactose (500 mg, 0.54 mmol) was acetylated using Ac$_2$O/pyridine and glacial acetic acid (93 μL, 1.62 mmol, 3.0 equiv.). The reaction mixture was stirred under rt for 5 d until the starting material was completely consumed. The reaction mixture was purified using flash column chromatography (EA/Hex/NEt$_3$ [ethyl acetate/hexanes/triethylamine]=5:85:10-14:85:1-29:70:1) to afford compounds 1, 2 and 3 (Table 1, Entry 1). Di-acetylated compound 1 (94 mg, 19%) was obtained as a white amorphous foam. TLC (EA/Hex=30:70) R$_f$ 0.70. $^1$H NMR (800 MHz, CDCl$_3$) δ 4.99 (d, J=3.1 Hz, 1H, H-1), 4.37-4.33 (m, 2H, H-6ab), 4.24 (dd, J=5.8, 10.7 Hz, 1H, H-6'a), 4.08 (dd, J=7.8, 10.7 Hz, 1H, H-6'b), 4.04 (d, J=7.5 Hz, 1H, H-1'), 4.02-3.97 (m, 1H, H-5), 3.74 (t, J=8.8 Hz, 1H, H-3), 3.71 (d, J=2.3 Hz, 1H, H-4'), 3.63 (app t, J=7.5, 9.2 Hz, 1H, H-2'), 3.50-3.45 (m, 2H, H-4, H-5'), 3.41 (dd, J=3.2, 9.0 Hz, 1H, H-2), 3.32 (dd, J=2.5, 9.2 Hz, 1H, H-3'), 2.09 (s, 3H), 2.05 (s, 3H), 0.13 (m, 54H). $^{13}$C NMR (200 MHz, CDCl$_3$) δ 170.90, 170.62, 103.0, 93.8, 77.0, 75.1, 74.0, 72.3, 71.93, 71.79, 71.51, 68.9, 63.28, 62.73, 21.1, 20.95, 0.91, 0.87, 0.60, 0.53, 0.49, 0.16. ESI-HRMS calcd. for C$_{34}$H$_{74}$O$_{13}$Si$_6$ [M+NH$_4$]$^+$: 876.4089. Found: 876.4090.

Example 1.2

(6-O-Acetyl-2,3,4-tri-O-trimethylsilyl-β-D-galactopyranosyl)-(1-4)-O-(1,6-di-O-acetyl-2,3-di-O-trimethylsilyl)-D-glucopyranoside (2)

Compound 2 (228 mg, 55%) was obtained as a white amorphous foam (Table 1, Entry 1). TLC (EA/Hex=3:7) R$_f$ 0.60. $^1$H NMR (800 MHz, CDCl$_3$) δ 5.42 (d, J=7.7 Hz, 1H, H-1), 4.42 (dd, J=2.0, 11.9 Hz, 1H, H-6a), 4.29 (dd, J=5.6, 12.0 Hz, 1H, H-6b), 4.24 (dd, J=6.0, 10.8 Hz, 1H, H-6'a), 4.07 (dd, J=7.4, 10.8 Hz, 1H, H-6'b), 4.03 (d, J=7.5, 1H, H-1'), 3.71 (d, J=2.3 Hz, 1H, H-4'), 3.65 (app t, J=7.5, 9.1 Hz, 1H, H-2'), 3.62-3.57 (m, 1H, H-5), 3.57-3.44 (m, 4H, H-2, H-3, H-4, H-5'), 3.30 (dd, J=2.5, 9.2 Hz, 1H, H-3'), 2.12 (s, 3H), 2.08 (s, 3H), 2.06 (s, 3H), 0.17-0.13 (m, 27H), 0.098 (s, 9H), 0.089 (s, 9H). $^{13}$C NMR (150 MHz, CDCl$_3$) δ 170.71, 170.65, 169.4, 103.0, 94.3, 76.16, 76.12, 75.2, 74.23, 74.14, 72.1, 71.51, 71.50, 62.75, 62.68, 21.41, 21.06, 20.94, 1.1, 0.96, 0.94, 0.60, 0.52. ESI-HRMS calcd. for C$_{33}$H$_{68}$O$_{14}$Si$_5$ [M+NH$_4$]$^+$: 846.3799. Found: 846.3828.

Example 1.3

(6-O-Acetyl-2,3,4-tri-O-trimethylsilyl-β-D-galactopyranosyl)-(1-4)-O-(1,2,6-tri-O-acetyl-3-O-trimethylsilyl)-D-glucopyranoside (3)

Compound 3 (50 mg, 12%) was obtained as a white amorphous foam (Entry 1, Table 1). TLC (EA/Hex=3:7) R$_f$ 0.28. $^1$H NMR (600 MHz, CDCl$_3$) δ 5.59 (d, J=8.4 Hz, 1H, H-1), 4.99-4.93 (m, 1H, H-2), 4.47 (dd, J=2.0, 12.0 Hz, 1H, H-6a), 4.28 (dd, J=5.3, 12.0 Hz, 1H, H-6b), 4.17 (dd, J=6.2, 10.9 Hz, 1H, H-6'a), 4.11 (dd, J=6.9, 10.9 Hz, 1H, H-6'b), 4.06 (d, J=7.5 Hz, 1H, H-1'), 3.71-3.67 (m, 3H, H-3, H-5, H-4'), 3.63-3.60 (m, 2H, H-2', H-4), 3.49 (t, J=6.5 Hz, 1H, H-5'), 3.31 (dd, J=2.5, 9.2 Hz, 1H, H-3'), 2.09 (s, 3H), 2.08 (s, 3H), 2.07 (s, 3H), 2.06 (m, 3H), 0.15 (s, 9H), 0.11 (s, 9H), 0.10 (s, 18H). $^{13}$C NMR (150 MHz, CDCl$_3$) δ 170.69, 170.62, 169.50, 169.42, 102.8, 92.3, 75.68, 75.12, 74.44, 73.76, 72.96, 72.37, 71.70, 71.62, 62.97, 62.37, 21.14, 21.07, 20.99, 20.98, 0.96, 0.62, 0.59, 0.53. ESI-HRMS calcd. for C$_{32}$H$_{62}$O$_{15}$Si$_4$ [M+NH$_4$]$^+$: 816.3510. Found: 816.3488.

Example 1.4

(2,3,6-Tri-O-acetyl-4-O-trimethylsilyl-β-D-galactopyranosyl)-(1-4)-O-(1,2,3,6-tetra-O-acetyl)-D-glucopyranoside (4)

Following the general procedure described above, per-O-TMS lactose (500 mg, 0.54 mmol) was acetylated using Ac$_2$O/pyridine and glacial acetic acid (216 μL, 3.78 mmol, 7.0 equiv.) followed by nine microwave irradiation cycles (standard mode, 100 W, 125° C., ~40 psi, 25 min). The reaction mixture was purified using flash column chromatography (EA/Hex=20:80-50:50) to afford compounds 4 and 5 (Table 1, Entry 7). Mono-silylated compound 4 (69 mg, 18%) was obtained as a white amorphous foam. TLC (EA/Hex=5:5) R$_f$ 0.34. $^1$H NMR (600 MHz, CDCl$_3$) δ 6.24 (d, J=3.7 Hz, 2H, H-1$_α$), 5.66 (d, J=8.3 Hz, 1H, H-1$_β$), 5.45 (app t, J=9.6, 10.2 Hz, 1H, H-3$_α$), 5.22 (t, J=9.2 Hz, 1H, H-3$_β$), 5.16-5.12 (m, 2H, H-2'$_α$, H-2'$_β$), 5.03 (dd, J=8.4, 9.3 Hz, 1H, H-2$_β$), 4.99 (dd, J=3.7, 10.3 Hz, 1H, H-2$_α$), 4.85-4.80 (m, 2H, H-3'$_α$, H-3'$_β$), 4.47-4.41 (m, 4H, H-1'$_α$, H-1'$_β$, H-6$_β$), 4.26-4.21 (m, 2H, H-6$_α$, H-6$_β$), 4.10-4.07 (m, 2H, H-6'$_α$, H-6'$_β$), 4.05-3.97 (m, 5H, H-6'$_α$, H-4'$_α$, H-5$_α$, H-6'$_β$, H-4'$_β$), 3.83-3.78 (m, 2H, H-4$_α$, H-4$_β$), 3.74 (ddd, J=2.0, 5.0, 9.9 Hz, 1H, H-5$_β$), 3.66-3.63 (m, 2H, H-5'$_α$, H-5'$_β$), 2.16 (s, 3H), 2.11 (s, 3H), 2.10 (s, 3H), 2.09 (s, 3H), 2.09 (s, 3H), 2.06 (s, 3H), 2.05 (s, 3H), 2.04 (s, 3H), 2.03 (s, 3H), 2.02 (s, 3H), 2.015 (s, 3H), 2.00 (s, 3H), 0.12 (s, 9H), 0.117 (s, 9H). $^{13}$C NMR (150 MHz, CDCl$_3$) δ 170.50, 170.48, 170.47, 170.46, 170.32, 170.10, 169.85, 169.72, 169.33, 169.24, 169.09, 169.00, 101.3, 101.1, 91.7, 89.2, 75.58, 75.49, 73.67, 73.53, 73.50, 72.81, 72.34, 72.33, 71.0, 70.7, 69.8, 69.7, 69.64, 69.60, 68.1, 62.00, 61.82, 61.77, 61.71, 21.08, 20.98, 20.90, 20.85, 20.7, 0.32, 0.32. ESI-HRMS calcd. for C$_{29}$H$_{44}$O$_{18}$Si [M+NH$_4$]$^+$: 726.2641. Found: 726.2639.

Example 1.5

(2,3,4,6-Tetra-O-acetyl-β-D-galactopyranosyl)-(1-4)-O-(1,2,3,6-tetra-O-acetyl-)-D-glucopyranoside (5)

Compound 5 (224 mg, 61%) was obtained as a white amorphous foam (Table 1, Entry 7). TLC (EA/Hex=5:5) R$_f$ 0.18. $^1$H NMR (600 MHz, CDCl$_3$) δ 6.25 (d, J=3.7 Hz, 1H), 5.66 (d, J=8.3 Hz, 1H), 5.47 (app t, J=9.6, 10.2 Hz, 1H), 5.38-5.31 (m, 2H), 5.24 (t, J=9.2 Hz, 1H), 5.11 (ddd, J=8.0, 9.1, 10.3 Hz, 2H), 5.04 (dd, J=8.3, 9.4 Hz, 1H), 5.00 (dd, J=3.7, 10.3 Hz, 1H), 4.95 (ddd, J=3.5, 9.1, 10.4 Hz, 2H), 4.51-4.39 (m, 5H), 4.18-4.04 (m, 7H), 4.00 (ddd, J=2.0, 4.1, 10.1 Hz, 1H), 3.87 (app dd, J=6.6, 12.5 Hz, 3H), 3.85-3.78 (m, 2H), 3.75 (ddd, J=2.0, 4.8, 9.9 Hz, 1H), 2.07 (m, 61H). $^{13}$C NMR (150 MHz, CDCl$_3$) δ 170.50, 170.47, 170.45, 170.42, 170.27, 170.26, 170.20, 170.19, 170.06, 169.75, 169.73, 169.70, 169.26, 169.14, 169.06, 168.99, 101.4, 101.1, 91.6, 89.1, 75.94, 75.80, 73.6, 72.7, 71.12, 71.08, 70.85, 70.61, 69.71, 69.23, 69.09, 66.70, 66.69, 61.85, 61.56, 60.95, 60.89, 21.00, 20.99, 20.82, 20.80, 20.80, 20.78, 20.76, 20.75, 20.65. ESI-MS calcd. for C$_{28}$H$_{38}$O$_{19}$ [M+NH$_4$]$^+$: 696.2351. Found: 696.2346.

Example 2

Figure 2:
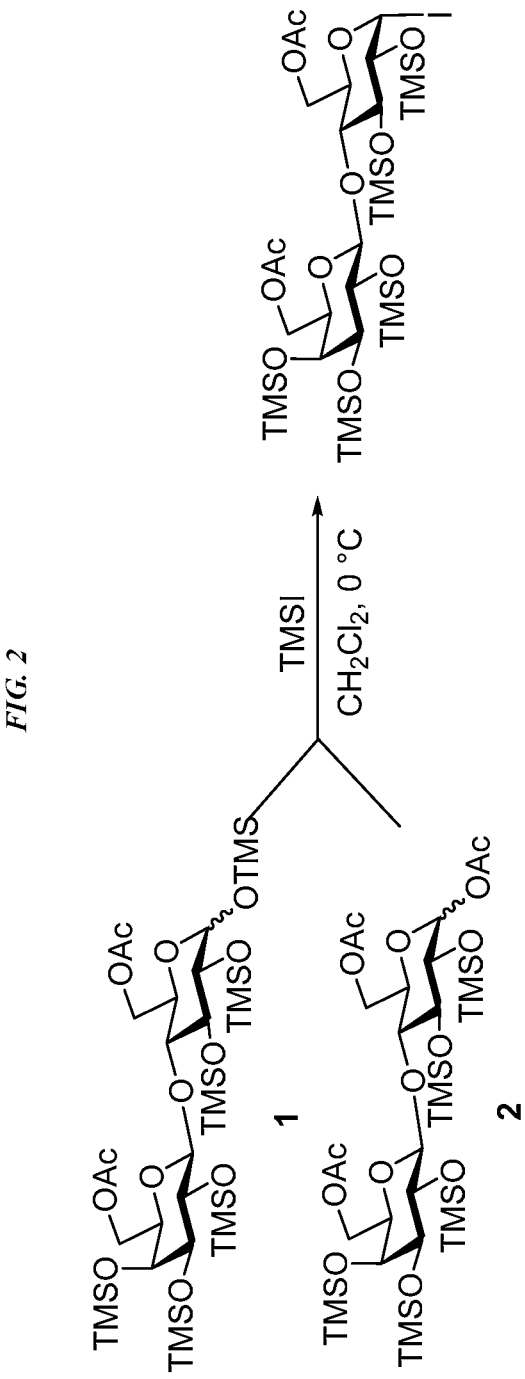
FIG. 2 shows the convergent preparation of a glycosyl iodide from differentially acetylated disaccharides 1 and 2.

Preparation of Diverse Synthetic Targets Using Selectively-Acylated Oligosaccharides Ready access to compounds 1-4 makes a wide range of glycosyl donors available with minimal synthetic manipulation because anomeric acetates can be selectively hydrolyzed rendering the 1-O-acetate orthogonal to other acetates. Moreover, activation of a mixture of 1 and 2 with TMSI provides the same lactosyl iodide (FIG. 2). The convergence of 1 and 2 to the same donor in situ gives an additive yield of 73% (Table 1, Entry 5) with respect to preparing the corresponding lactosyl iodide.

Figure 3:
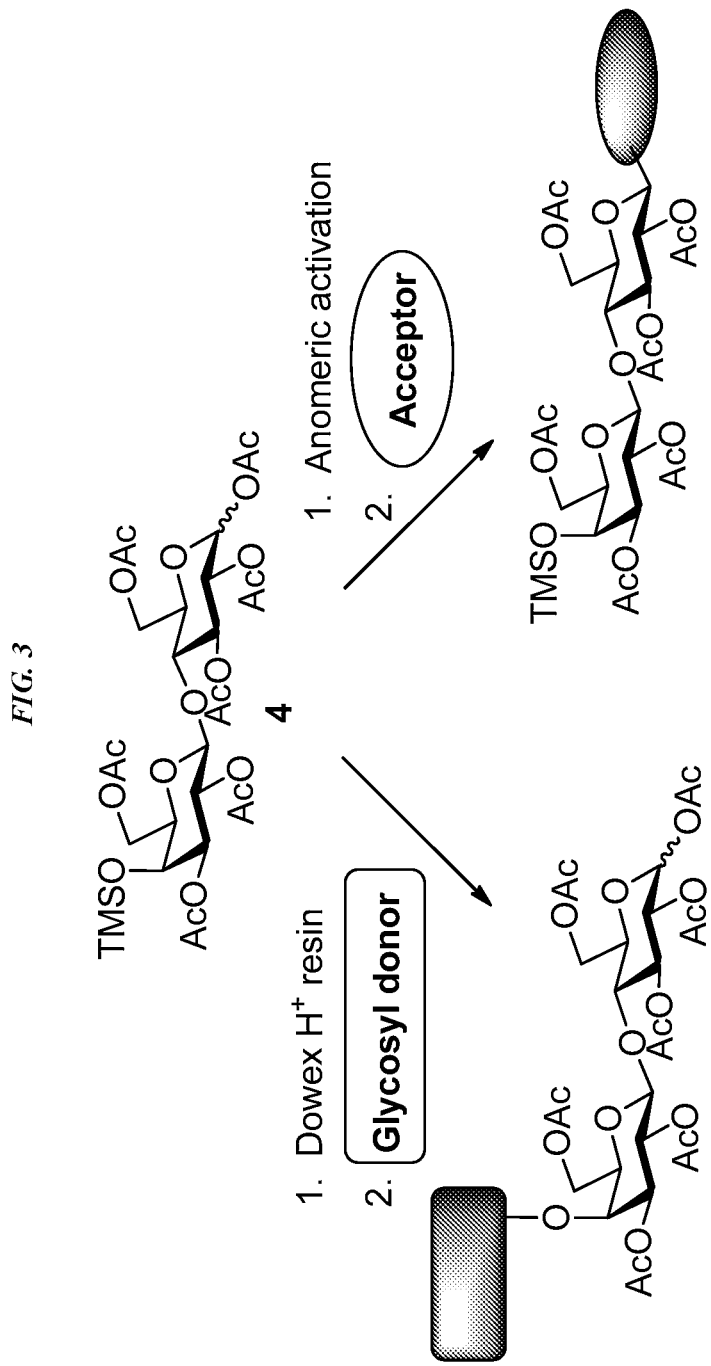
FIG. 3 shows the bifunctional nature of orthogonally protected lactose 4 as a synthetic substrate.

Compound 4, containing a single TMS ether at the 4' position, is poised for use as a glycosyl donor or acceptor in one synthetic step (FIG. 3). As shown in FIG. 3, the anomeric acetate can be readily transformed into a reactive glycosyl iodide donor. In addition to serving as a glycosyl donor, selectively acetylated lactose can also function as a glycosyl acceptor after removal of the silyl protecting groups. In this manner, the bifunctional molecule (4) is poised to serve as a modular building block for more complex oligosaccharides such as P$^k$ trisaccharide, which is a common structural feature of Gb3, Gb5 and globo H.

Figure 4:
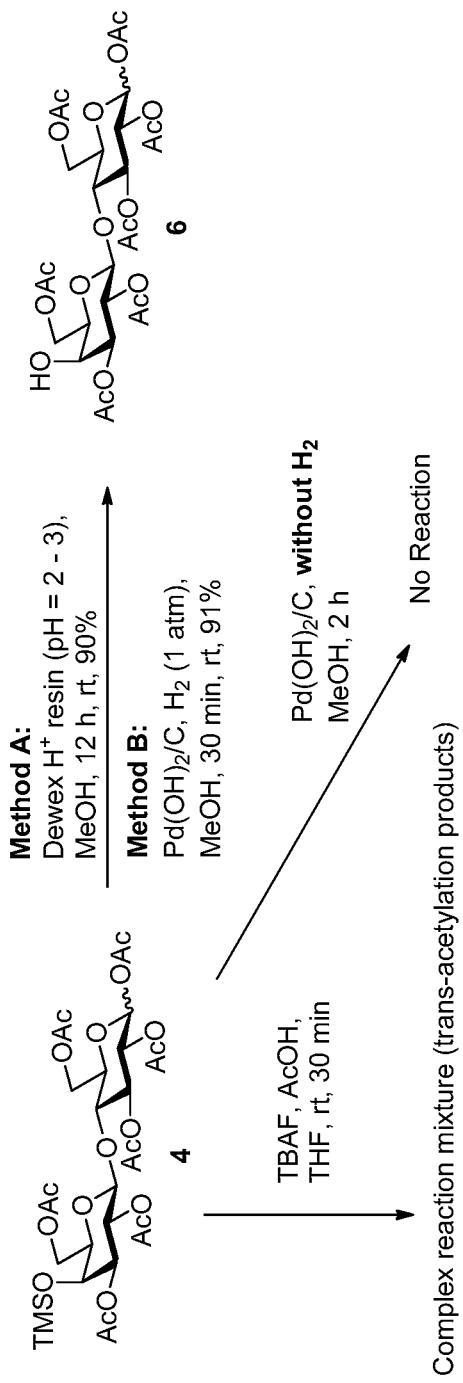
FIG. 4 shows a summary of silyl group reactivity for orthogonally protected lactose 4; removal of the TMS protecting group proceeded cleanly using acidic resin or Pd-catalyzed hydrogenolysis, but the use of TBAF with acetic acid resulted in trans-acetylation products.

In order to reveal the selectively protected lactosyl acceptor (6), compound 4 was treated with Dowex acidic resin. After 12 h, TLC showed the disappearance of starting material and the key intermediate (6) was obtained in 90% yield (FIG. 4). It was somewhat surprising that desilylation required 12 h. In previous studies, the inventors found that as the number of acetate protecting groups increase, the time required for desilylation also increases. Without wishing to be bound by any particular theory, it appears that the electronic nature of the acetate groups inductively stabilizes the silyl protecting groups, which may also impact regiocontrol of exchange. In order to shorten the reaction time, compound 4 was also treated with traditional TBAF/AcOH conditions, but, unfortunately, the reaction led to trans-acetylation products which were confirmed by NMR analysis. Meanwhile, Pd-catalyzed hydrogenolysis was also applied to compound 4. Within 30 min, compound 4 was transformed to 6 under 1 atm $H_2$ atmosphere in 91% yield.

Because the trimethylsilyl protecting groups are stable for extended periods of time, this selective acetylation process enables the large-scale synthesis of partially protected silyl sugars without concern of trans-acetylation.

Figure 5:
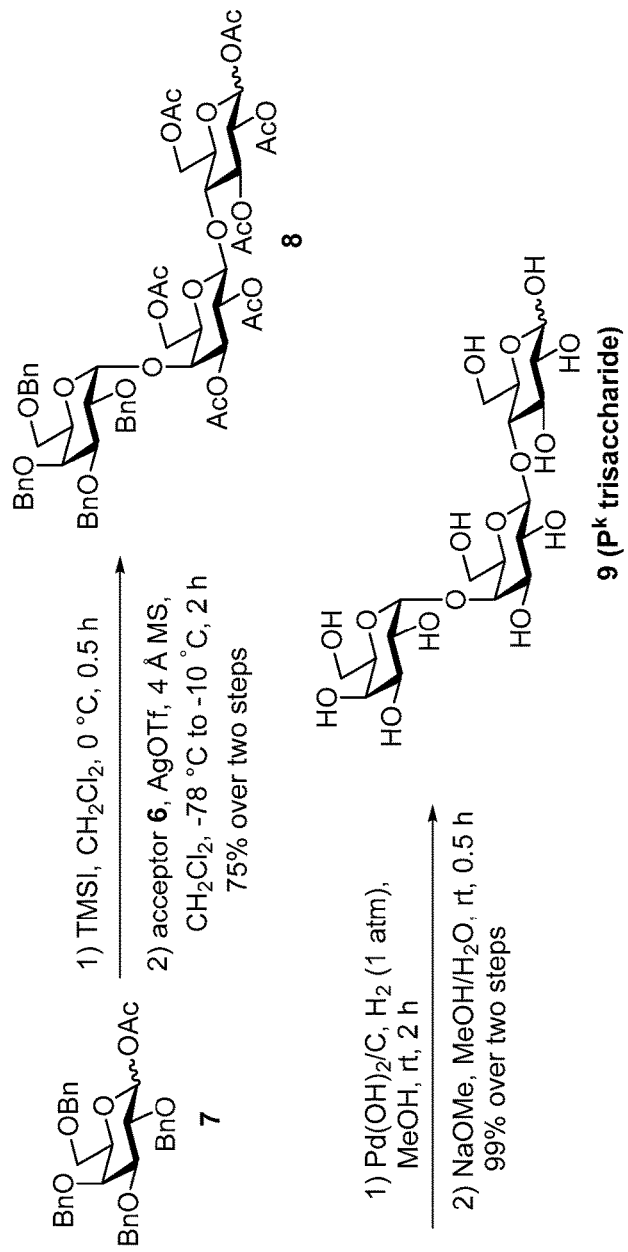
FIG. 5 shows the synthesis of P$^k$ trisaccharide using glycosyl acceptor 6.
Figure 6:
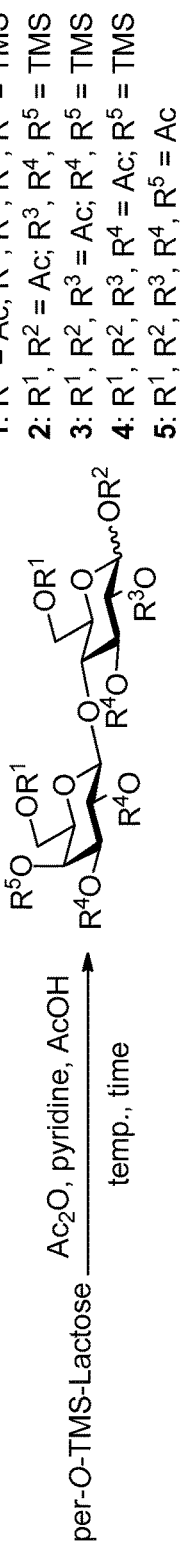
FIG. 6 shows the selective acetylation of per-O-TMS lactose according to the methods of the invention.

Elaboration of the lactosyl acceptor continued with galactosylation of the 4' hydroxyl using the glycosyl iodide derived from anomeric acetate 7. The iodide was transferred into a cooled, well-stirred $CH_2Cl_2$ solution containing 6, silver triflate (AgOTf), and activated molecular sieves under inert atmosphere. The reaction mixture was allowed to warm from −78° C. to −10° C. over 2 h and was quenched with triethylamine followed by filtration through a celite pad. After extraction, concentration, and purification using flash column chromatography, the resulting protected Pk trisaccharide (8) was obtained in 75% yield. Only the desired α-1,4 linkage was obtained and the corresponding β-1,4 linked isomer was not observed in NMR experiments of the crude reaction mixture. Global deprotection of compound 8 continued with palladium-catalyzed hydrogenolysis followed by deacetylation, yielding $P^k$ trisaccharide (9) in nearly quantitative yield (FIG. 5).

Example 2.1

(2,3,6-Tri-O-acetyl-4-ol-β-D-galactopyranosyl)-(1-4)-O-(1,2,3,6-tetra-O-acetyl)-D-glucopyranoside (6)

Method A: To a MeOH (2 mL) solution of compound 4 (63 mg, 0.09 mmol) was added Dowex H+ resin (~250 mg). The suspension was allowed to stir at rt until TLC showed the starting material was completely consumed (12 h). Next, the resin was removed via filtration and the solution was concentrated to afford a viscous oil. The crude mixture was immediately purified using flash column chromatography (EA/Hex=70:30) to obtain compound 6 (50 mg, 90%) as a white amorphous foam. Method B: To a MeOH solution (4 mL) of compound 4 (130 mg, 0.18 mmol) was added Pd(OH)$_2$/C (20% Pd, 63 mg) and stirred under $H_2$ gas (1 atm balloon) for 0.5 h. After the disappearance of starting material on TLC, the Pd(OH)$_2$/C was removed by passing the reaction mixture through a MeOH-packed celite pad. The filtrate was concentrated and the residue was purified using flash column chromatography (EA/Hex=67:33-50:50) to obtain 6 (106 mg, 91%) as a white amorphous foam. TLC (EA/Hex=2:1) $R_f$ 0.27. $^1$H NMR (800 MHz, CDCl$_3$) δ 6.25 (d, J=3.7 Hz, 1H, H-1$_\alpha$), 5.66 (d, J=8.3 Hz, 1H, H-1$_\beta$), 5.44 (t, J=9.8 Hz, 1H, H-3$_\alpha$), 5.23 (t, J=9.2 Hz, 1H, H-3$_\beta$), 5.18-5.14 (m, 2H, H-2'$_\alpha$, H-2'$_\beta$), 5.05 (app t, J=8.4, 9.0 Hz, 1H, H-2$_\beta$), 5.01 (dd, J=3.7, 10.3 Hz, 1H, H-2$_\alpha$), 4.92-4.84 (m, 2H, H-3'$_\alpha$, H-3'$_\beta$), 4.48-4.41 (m, 4H, H-1'$_\alpha$, H-6a$_\alpha$, H-1'$_\beta$, H-6a$_\beta$), 4.33-4.23 (m, 4H, H-6'ab$_\alpha$, H-6'ab$_\beta$), 4.13-4.11 (m, 2H, H-6b$_\alpha$, H-6 b$_\beta$), 4.01-3.98 (m, 3H, H-4'$_\alpha$, H-5$_\alpha$, H-4'$_\beta$,), 3.83-3.79 (m, 2H, H-4$_\alpha$, H-4$_\beta$), 3.77-3.75 (m, 1H, H-5$_\beta$), 3.71-3.69 (m, 2H, H-5'$_\alpha$, H-5'$_\beta$), 2.46 (s, 2H), 2.17 (s, 3H), 2.14-1.98 (m, 43H). $^{13}$C NMR (200 MHz, CDCl$_3$) δ 170.91, 170.88, 170.49, 170.45, 170.18, 170.07, 169.98, 169.95, 169.68, 169.44, 169.36, 169.08, 169.00, 101.2, 101.0, 91.7, 89.1, 75.9, 75.7, 73.7, 73.42, 73.37, 72.7, 72.23, 72.18, 70.9, 70.6, 69.7, 69.6, 69.5, 66.9, 66.8, 62.03, 62.00, 61.97, 61.7, 21.08, 21.00, 20.98, 20.96, 20.94, 20.90, 20.83, 20.77, 20.74, 20.65. ESI-HRMS calcd. for $C_{26}H_{36}O_{18}$ [M+NH$_4$]$^+$: 654.2245. Found: 654.2243.

Example 2.2

(2,3,4,6-Tetra-O-benzyl-α-D-galactopyranosyl)-(1-4)-O-(2,3,6-tri-O-acetyl-β-O-D-galactopyranosyl)-(1-4)-O-1,2,3,6-tetra-O-acetyl-D-glucopyranoside (8)

To a 0° C. CH$_2$Cl$_2$ solution (4 mL) of compound 7 (510 mg, 0.88 mmol) was added TMSI (142 μL, 0.97 mmol) under argon atmosphere. After stirring for 30 min, the reaction mixture was quenched by adding anhydrous benzene (5 mL) and concentrated under reduced pressure. After co-evaporating with anhydrous benzene three times, the corresponding glycosyl iodide was obtained as a yellowish amorphous foam. The iodide was then dissolved in CH$_2$Cl$_2$ (2 mL) under argon and cooled to −78 OC. In a separate round bottom flask, AgOTf (270 mg, 1.05 mmol), 4'-OH acceptor 6 (220 mg, 0.35 mmol), and activated 4 Å molecular sieves were allowed to stir in a CH$_2$Cl$_2$ (3 mL) solution under argon atmosphere at rt for 30 min. The acceptor solution was cooled to −78° C. and the cooled glycosyl iodide solution was transferred dropwise to the acceptor flask via cannula. After 2 h, TLC revealed complete consumption of the acceptor. The reaction mixture was gradually warmed to −20 OC, diluted with EA (10 mL) and quenched by adding NEt$_3$ (1 mL). The suspension was filtered through a well-packed celite pad and washed with EA (~30 mL). The filtrate was washed with saturated NaS$_2$O$_{3(aq)}$ (20 mL×1), NaHCO$_{3(aq)}$ (20 mL×1) and brine (20 mL×2), dried over anhydrous Na$_2$SO$_4$(s) and concentrated under reduced pressure. The resulting residue was purified using gradient flash column chromatography (EA/Hex=40:60-50:50) to obtain 8 (300 mg, 75%) as a white amorphous foam. TLC (EA/Hex=1/1) $R_f$ 0.43. The products consisted of anomeric acetates (α/β=1/3.2). The major 3-anomer is reported: $^1$H NMR (800 MHz, CDCl$_3$) δ 7.43-7.24 (m, 20H, ArH), 5.65 (d, J=8.3 Hz, 1H, H-1), 5.20 (t, J=9.3 Hz, 1H, H-3), 5.13 (dd, J=10.2, 8.1 Hz, 1H, H-2'), 5.04 (t, J=8.9 Hz, 1H, H-2), 4.92 (d, J=12.0 Hz, 1H, PhCH), 4.82 (d, J=4.1 Hz, 1H, H-3"), 4.76-4.73 (m, 4H, H-1", H-3', PhCH×2), 4.67 (d, J=12 Hz, 1H, PhCH), 4.56 (d, J=12 Hz, 1H, PhCH), 4.50-4.40 (m, 4H, H-6a, H6'ab, PhCH×2), 4.39 (d, J=7.8 Hz, 1H, H-1'), 4.27 (dd, J=9.0, 4.7 Hz, 1H, H-5"), 4.16 (s, 1H, H-4"), 4.10 (dd, J=12.3, 4.6 Hz, 1H, H6b), 4.05 (m, 1H, H-2"), 3.97 (d, J=2.3, 1H), 3.77 (t, J=8.9 Hz, 1H, H-4), 3.72 (dd, J=10.0, 4.7 Hz, 1H, H-5), 3.64 (t, J=6.8 Hz, 1H, H5'), 3.61 (t, J=8.9 Hz, 1H, H6"a), 3.42 (dd, J=8.3, 4.9 Hz, 1H, H-6"b), 2.11 (s, 3H), 2.09 (s, 3H), 2.04 (s, 6H), 2.03 (s, 3H), 2.02 (s, 3H), 1.86 (s, 3H), 1.85 (s, 3H). $^{13}$C NMR (200 MHz, CDCl$_3$) 3170.7, 170.4, 170.3, 169.8, 169.5, 168.9, 168.7, 138.8, 138.7, 138.1, 137.9, 128.4, 128.33, 128.30, 128.2, 128.15, 128.11, 128.0, 127.7, 127.6, 127.4, 127.36, 127.34, 101.4, 101.0, 91.7, 79.1, 76.0, 75.5, 75.3, 75.0, 74.6, 74.2, 73.6, 73.3, 72.8, 72.5, 72.3, 72.2, 70.3, 69.6, 69.4, 67.6, 61.7, 61.0, 20.84, 20.82, 20.6, 20.5. ESI-HRMS calcd. for $C_{60}H_{70}O_{23}$ [M+NH$_4$]$^+$: 1181.4200. Found: 1181.4241.

Example 2.3

α-D-galactopyranosyl-(1-4)-β-D-galactopyranosyl-(1-4)-D-glucopyranose (9)

To a MeOH solution (5 mL) of compound 8 (63 mg, 0.054 mmol) was added Pd(OH)$_2$/C (20% Pd, 63 mg) and stirred under H$_2$ gas (1 atm) for two hours. After the disappearance of starting material on TLC, the Pd(OH)$_2$/C was removed by passing through a MeOH-packed celite pad. The filtrate was concentrated and re-dissolved in anhydrous MeOH (3 mL) followed by addition of NaOMe/MeOH solution (25% wt, 40 µL). Some white suspension formed after 15 min and H$_2$O (1.0 mL) was added to dissolve the suspension. The reaction mixture was stirred for another 15 min and was acidified to pH=6 by adding Dowex acidic resin. The solution was filtered through a plug of C18 reverse-phrase silica gel and washed with MeOH and water to remove the resin and desalt. The filtrate was concentrated and lyophilized to afford compound 9 (27 mg, 99%) as a white fluffy foam. TLC (EA/2-propanol/H$_2$O=2:2:1) R$_f$ 0.22. $^1$H NMR (800 MHz, D$_2$O) δ 5.22 (d, J=3.7 Hz, 0.4H), 4.94 (d, J=3.7 Hz, 1H), 4.66 (d, J=8.0 Hz, 0.4H), 4.50 (dd, J=7.8, 1.7 Hz, 1H), 4.35 (s, 1H), 4.06-4.01 (m, 2H), 3.98-3.54 (m, 14H), 3.27 (t J=8.6 Hz, 0.4H). $^{13}$C NMR (200 MHz, D$_2$O) 103.90, 103.86, 101.0, 96.4, 92.4, 79.3, 79.2, 78.0, 75.5, 74.5, 72.8, 71.5, 70.8, 69.8, 69.6, 69.22, 69.20, 61.1, 61.0, 60.7, 60.6. (Assignment matches with literature). ESI-HRMS calcd. for C$_{18}$H$_{32}$O$_{16}$ [M+NH$_4$]$^+$: 522.2029. Found: 522.2012.

Example 3

Regioselective Acylation of Per-O-Silylated Melibiose

Melibiose (D-galactopyranosyl-α(1-6)-D-glucopyranoside), which is a disaccharide composed of the same monomeric units as lactose but having a different glycosidic linkage, was chosen to examine the reactivity differences between these constitutional isomers (Table 2). Per-O-TMS melibiose was prepared in one step from commercially available melibiose by known methods and acylated starting with 2.0 equiv. of glacial acetic acid. The reaction mixture was subjected to microwave irradiation at 125° C. for six 25 min cycles and followed by TLC. Purification of the reaction mixture afforded 6'-mono-O-acetate (10) and 1,6'-di-O-acetate (11) as a mixture of a/13 anomers (Table 2, Entry 1). Increasing the acetic acid to 7.0 equiv. resulted in the formation of penta- to per-O-acetates (12-15), which were isolated in moderate yields (Table 2, Entry 2). These were also found to be a mixture of a/3 anomers.

While the lactosyl products always contained 10-15% unresolved partially acetylated compounds besides the major products, the melibiose system yielded well-resolved partially acetylated intermediates. NMR analysis showed the melibiose intermediates were distinctive acetylation products, suggesting the acetylation proceeded in a more stepwise fashion than the lactosyl system. More interestingly, after the primary and anomeric position were acetylated, the glucosyl moiety was the next part to be acetylated followed by the 2', 3' and finally 4' position of the galactosyl moiety. This process enabled the first reported synthesis of these selectively acetylated melibiose species (12-15) which might be useful for the synthetic and biological community.

TABLE 2

Selective acetylation of per-O-TMS melibiose.

per-O-TMS-melibiose $\xrightarrow{\text{Ac}_2\text{O, pyridine, AcOH}}_{\text{temp., time}}$

[Structure showing sugar with substituents R$^1$O, R$^2$O, R$^3$O, R$^4$O, R$^5$O, R$^6$O]

10. R$^1$ = Ac; R$^2$, R$^3$, R$^4$, R$^5$, R$^6$ = TMS
11. R$^1$, R$^2$ = Ac; R$^3$, R$^4$, R$^5$, R$^6$ = TMS
12. R$^1$, R$^2$, R$^3$ = Ac; R$^4$, R$^5$, R$^6$ = TMS
13. R$^1$, R$^2$, R$^3$, R$^4$ = Ac; R$^5$, R$^6$ = TMS
14. R$^1$, R$^2$, R$^3$, R$^4$, R$^5$ = Ac; R$^6$ = TMS
15. R$^1$, R$^2$, R$^3$, R$^4$, R$^5$, R$^6$ = Ac

| Entry | AcOH (equiv.) | Temp. | Time | Product Distribution (Yield) | | | |
|---|---|---|---|---|---|---|---|
| 1 | 2 | µwave, 125° C. | 2.5 h | 10 (39%) | 11 (20%) | | |
| 2 | 7 | µwave, 125° C. | 2.5 h | | 12 (7%) | 13 (26%) | 14 (22%) 15 (44%) |

Example 3.1

(2,3,4-Tri-O-trimethylsilyl-6-O-acetyl-α-D-galactopyranosyl)-(1-6)-O-(1,2,3,4-tetra-O-trimethylsilyl)-α-D-glucopyranoside (10)

Following the general procedure described above, per-O-TMS melibiose (500 mg, 0.54 mmol) was acetylated using Ac$_2$O/pyridine and glacial acetic acid (62 µL, 1.08 mmol, 2 equiv.) followed by six irradiation cycles (standard mode, 100 W, 125° C., ~40 psi, 25 min). The reaction mixture was purified using flash column chromatography (EA/Hex=5: 95-12:88) to afford compounds 10 and 11 (Table 2, Entry 1). Mono-acetylated analogue 10 (1 90 mg, 39%) was obtained as a white foam. TLC (EA/Hex=15:85) R$_f$ 0.59. $^1$H NMR (800 MHz, CDCl$_3$) δ 5.07 (d, J=3.4 Hz, 1H, H-1'), 4.92 (d, J=3.0, 1H, H-1), 4.17-4.10 (m, 2H, H-6'ab), 3.88-3.64 (m, 9H, H-3, H-4, H-5, H-6ab, H-2', H-3', H-4', H-5'), 3.33 (dd, J=3.1, 9.1 Hz, 1H, H-2), 2.06 (s, 3H), 0.20 (s, 9H), 0.14 (s, 9H), 0.13 (s, 9H), 0.127 (s, 9H), 0.122 (s, 9H), 0.121 (s, 9H), 0.11 (s, 9H). $^{13}$C NMR (200 MHz, CDCl$_3$) δ 170.8, 99.6, 93.8, 74.3, 74.2, 72.9, 72.82, 71.82, 70.6, 69.2, 68.6, 63.7, 21.0, 1.4, 1.1, 0.69, 0.63, 0.53, 0.33, 0.30. ESI-HRMS calcd. for C$_{35}$H$_{80}$O$_{12}$Si$_7$ [M+NH$_4$]$^+$=906.4378. Found: 906.4390.

Example 3.2

(2,3,4-Tri-O-trimethylsilyl-6-O-acetyl-α-D-galactopyranosyl)-(1-6)-O-(2,3,4-tri-O-trimethylsilyl-1-O-acetyl)-D-glucopyranoside (11)

Compound 11 (90 mg, 20%) was obtained as a white foam (Table 2, Entry 1). TLC (EA/Hex=15:85) R$_f$ 0.40. $^1$H NMR (800 MHz, CDCl$_3$) δ 6.02 (d, J=3.5 Hz, 4H, H-1$_\alpha$), 5.33 (d, J=8.0 Hz, 1H, H-1$_\beta$), 5.06 (d, J=3.4 Hz, 1H, H-1'$_\beta$), 5.00 (d, J=3.4 Hz, 4H, H-1'$_\alpha$), 4.15-4.07 (m, 12H, H-6ab), 3.90-3.63 (m, 50H, H-5, H-2', H-6', H-3', H-5', H-4', H-4, H-3, H-6'), 3.53 (dd, J=3.6, 9.0 Hz, 4H, H-3$_\alpha$), 3.45 (t, J=8.8 Hz, 1H), 3.42-3.39 (m, 1H), 3.36 (d, J=9.2 Hz, 1H), 2.08 (s, 12H), 2.07 (s, 4H), 2.07 (s, 13H), 2.05 (s, 3H), 0.21-0.11 (m, 313H). $^{13}$C NMR (200 MHz, CDCl$_3$) δ 170.9, 170.8, 169.7, 169.4, 99.7, 99.6, 94.5, 92.1, 78.1, 77.9, 75.4, 74.9, 74.2, 73.0, 72.9, 72.5, 70.9, 70.6, 70.5, 69.1, 69.1, 68.8, 68.7, 63.8, 63.7, 62.7, 62.1, 21.3, 21.2, 21.08, 21.06, 1.5, 1.4, 1.10, 1.05, 1.01, 0.7, 0.63, 0.60, 0.4, 0.31, 0.25, 0.2. ESI-HRMS calcd. for C$_{34}$H$_{74}$O$_{13}$Si$_6$ [M+NH$_4$]$^+$: 876.4089. Found: 876.4105.

Example 3.3

(2,3,4-Tri-O-trimethylsilyl-6-O-acetyl-α-D-galactopyranosyl)-(1-6)-O-(1,2,3,4-tetra-O-acetyl)-D-glucopyranoside (12)

Following the general procedure described above, per-O-TMS melibiose (500 mg, 0.54 mmol) was acetylated using Ac$_2$O/pyridine and glacial acetic acid (216 μL, 3.78 mmol, 7.0 equiv.) followed by six cycles of microwave irradiation (standard mode, 100 W, 125° C., ~40 psi, 25 min). The reaction mixture was purified using flash column chromatography (EA/Hex=40:60-60:40) to afford compounds 12, 13, 14 and 15 (Table 2, Entry 2). Penta-acetylated analogue 12 (21 mg, 7%) was obtained as a white foam. (EA/Hex=1/1) R$_f$ 0.81. $^1$H NMR (800 MHz, CDCl$_3$) δ 6.27 (d, J=3.7 Hz, 1H, H-1$_\alpha$), 5.64 (d, J=8.4 Hz, 1H, H-1$_\beta$), 5.46 (t, J=9.8 Hz, 1H, H-3$_\alpha$), 5.23 (t, J=9.4 Hz, 1H, H-3$_\beta$), 5.16 (td, J=6.2, 9.8, 2H, H-4$_\alpha$, H-4$_\beta$), 5.09 (app t, J=8.0, 9.6 Hz, 1H, H-2$_\beta$), 5.03 (dd, J=3.7, 10.3 Hz, 1H, H-2$_\alpha$), 4.75 (d, J=3.2 Hz, 1H, H-1'$_\beta$), 4.73 (d, J=4.0 Hz, 1H, H-1'$_\alpha$), 4.13 (dd, J=5.6, 11.2 Hz, 1H, H-6'$_\beta$), 4.15-4.08 (m, 3H, H-6'$_\alpha$, H-6'$_\alpha$, H-5$_\beta$), 4.05 (dd, J=7.3, 11.2 Hz, 1H, H-6'$_\beta$), 3.91 (app t, J=6.4 Hz, 1H, H-5'$_\beta$), 3.90-3.85 (m, 3H, H-2'$_\alpha$, H-5'$_\alpha$, H-2'$_\beta$), 3.83 (m, 3H, H-5$_\alpha$, H-3'$_\alpha$, H-3'$_\beta$), 3.79 (d, J=1.2 Hz, 2H, H-4'$_\alpha$, H-4'$_\beta$), 3.70 (dd, J=5.3, 11.6 Hz, 2H, H-6$_\alpha$, H-6$_\beta$), 3.59 (dd, J=1.7, 11.6 Hz, 1H, H-6$_\beta$), 3.52 (dd, J=1.8, 11.5 Hz, 1H, H-6$_\alpha$), 2.16 (s, 3H), 2.07 (app d, J=3.0 Hz, 9H), 2.04 (s, 3H), 2.03 (app dd, J=3.3, 7.7 Hz, 12H), 2.01 (s, 3H), 0.17 (s, 9H), 0.16 (s, 9H), 0.14 (s, 9H), 0.13 (app d, J=1.1 Hz, 27H). $^{13}$C NMR (200 MHz, CDCl$_3$) δ 170.8, 170.5, 170.4, 169.9, 169.5, 169.4, 169.3, 169.1, 169.0, 99.9, 91.9, 89.1, 74.2, 73.3, 73.1, 72.9, 71.1, 70.5, 70.4, 70.3, 69.5, 69.3, 69.2, 69.0, 68.7, 68.5, 65.8, 65.5, 63.9, 63.7, 21.0, 20.9, 20.8, 20.8, 20.7, 0.72, 0.72, 0.60, 0.58, 0.43, 0.37. ESI-HRMS calcd. for C$_{31}$H$_{56}$O$_{16}$Si$_3$ [M+NH$_4$]$^+$: 786.3220. Found: 786.3183.

Example 3.4

(3,4-Di-O-trimethylsilyl-2,6-di-O-acetyl-α-D-galactopyranosyl)-(1-6)-O-(1,2,3,4-tetra-O-acetyl)-D-glucopyranoside (13)

Compound 13 (52 mg, 26%) was obtained as a white foam (Table 2, Entry 2). TLC (EA/Hex=1/1) R$_f$ 0.70. $^1$H NMR (800 MHz, CDCl$_3$) δ 6.26 (d, J=3.7 Hz, 3H, H-1$_\alpha$), 5.64 (d, J=8.3 Hz, 1H, H-1$_\beta$), 5.45 (t, J=9.9 Hz, 3H, H-3$_\alpha$), 5.22 (t, J=9.4 Hz, 1H, H-3$_\beta$), 5.17 (td, J=5.0, 9.8 Hz, 4H, H-4$_\alpha$, H-4$_\beta$), 5.11 (d, J=3.5, 4H, H-1'$_\alpha$, H-1'$_\beta$), 5.05 (app t, J=8.8, 9.6 Hz, 1H, H-2$_\beta$), 5.01 (dd, J=3.7, 10.3 Hz, 3H, H-2$_\alpha$), 4.90-4.85 (m, 4H, H-2'$_\alpha$, H-2'$_\beta$), 4.14-4.05 (m, 9H, H-6'$_\alpha$, H-6', H-6'$_\alpha$, H-6'$_\beta$), 4.03 (m, 7H, H-3'$_\alpha$, H-5$_\alpha$, H-3'$_\beta$), 3.85 (d, J=2.6 Hz, 3H, H-4'$_\alpha$), 3.84-3.79 (m, 6H, H-5'$_\alpha$, H-5'$_\beta$, H-4'$_\beta$), 3.73 (dd, J=2.6, 9.8 Hz, 1H, H-5$_\beta$), 3.66 (dt, J=5.4, 10.8 Hz, 4H, H-6$_\alpha$, H-6$_\beta$), 3.54 (dd, J=1.7, 11.8 Hz, 1H, H-6'$_\beta$), 3.49 (dd, J=1.7, 11.7 Hz, 3H, H-6'$_\alpha$), 2.17 (s, 8H), 2.14 (s, 3H), 2.10 (s, 9H), 2.09 (s, 4H), 2.06 (s, 12H), 2.04 (s, 9H), 2.03 (app d, J=3.1 Hz, 7H), 2.02 (app d, J=3.3 Hz, 18H), 2.00 (s, 4H), 0.18 (s, 10H), 0.17-0.16 (m, 25H), 0.11 (app d, J=3.4 Hz, 37H). $^{13}$C NMR (200 MHz, CDCl$_3$) δ 170.8, 170.74, 170.72, 170.69, 170.4, 170.3, 169.9, 169.5, 169.4, 169.3, 169.1, 168.96, 96.6, 96.2, 91.7, 89.1, 77.3, 77.2, 77.0, 73.8, 73.2, 72.5, 72.4, 71.42, 71.35, 70.5, 70.3, 70.2, 69.4, 69.0, 68.8, 68.5, 68.4, 68.2, 67.9, 64.9, 63.7, 63.5, 21.23, 21.22, 21.00, 20.90, 20.83, 20.75, 20.7, 20.6, 0.6, 0.50, 0.49. ESI-HRMS calcd. for C$_{30}$H$_{50}$O$_{17}$Si$_2$ [M+NH$_4$]$^+$ =756.2930. Found: 756.2903.

Example 3.5

(2,3,6-Tri-O-acetyl-4-O-trimethylsilyl-α-D-galactopyranosyl)-(1-6)-O-(1,2,3,4-tetra-O-acetyl)-D-glucopyranoside (14)

Compound 14 (43 mg, 22%) was obtained as a white foam (Table 2, Entry 2). TLC (EA/Hex=1/1) R$_f$ 0.55. $^1$H NMR (800 MHz, CDCl$_3$) δ 6.27 (d, J=3.6 Hz, 1H, H-1$_\alpha$), 5.66 (d, J=8.3 Hz, 1H, H-1$_\beta$), 5.46 (t, J=9.9 Hz, 1H, H-3$_\alpha$), 5.25-5.20 (m, 3H, H-3'$_\alpha$, H-3'$_\beta$, H-3$_\beta$), 5.18-5.09 (m, 6H, H-4$_\alpha$, H-2'$_\alpha$, H-1'$_\alpha$, H-4$_\beta$, H-2'$_\beta$, H-1'$_\beta$), 5.06 (app t, J=8.8, 9.6 Hz, 1H, H-2$_\beta$), 5.03 (dd, J=4.0, 10.4 Hz, 1H, H-2$_\alpha$), 4.17-4.10 (m, 4H, H-4'$_\alpha$, H-6'$_\alpha$, H-4'$_\beta$, H-6'$_\beta$), 4.04-4.06 (m, 1H, H-5$_\alpha$), 4.03-3.96 (m, 3H, H-6'$_\alpha$, H-5'$_\alpha$, H-6'$_\beta$), 3.94 (app t, J=6.5 Hz, 1H, H-5'$_\beta$), 3.78-3.74 (m, 1H, H-5$_\beta$), 3.70 (dd, J=4.5, 11.7 Hz, 2H, H-6$_\alpha$, H-6$_\beta$), 3.59 (dd, J=2.4, 11.7 Hz, 1H, H-6$_\beta$), 3.54 (dd, J=2.5, 11.5 Hz, 1H, H-6$_\alpha$), 2.18 (s, 3H), 2.11 (s, 3H), 2.09-2.08 (m, 12H), 2.06 (app d, 6H), 2.04-2.03 (m, 6H), 2.02 (app d, 6H), 2.00 (app d, 6H), 0.11 (app d, 18H). $^{13}$C NMR (200 MHz, CDCl$_3$) δ 170.76, 170.67, 170.6, 170.5, 170.4, 170.3, 170.2, 169.8, 169.5, 169.4, 169.09, 169.05, 96.5, 96.1, 91.7, 89.0, 73.5, 73.0, 70.5, 70.3, 70.0, 69.91, 69.4, 69.3, 69.2, 68.6, 68.4, 68.34, 68.26, 68.1, 65.7, 65.6, 64.5, 62.8, 62.6, 21.29, 21.27, 21.03, 20.95, 20.94, 20.90, 20.83, 20.75, 20.74, 20.73, 20.71, 20.6, 0.4. ESI-HRMS calcd. for C$_{29}$H$_{44}$O$_{18}$Si [M+NH$_4$]$^+$: 726.2641. Found: 726.2616.

Example 3.6

(2,3,4,6-Tetra-O-acetyl-α-D-galactopyranosyl)-(1-6)-O-(1,2,3,4-tetra-O-acetyl)-D-glucopyranoside (15)

Compound 15 (81 mg, 44%) was obtained as a white foam (Table 2, Entry 2). TLC (EA/Hex=1/1) R$_f$ 0.33. $^1$H NMR (800 MHz, CDCl$_3$) δ 6.25 (d, J=3.4 Hz, 1H), 5.64 (d, J=8.3 Hz, 1H), 5.46-5.39 (m, 4H), 5.30 (ddd, J=3.3, 6.7, 10.2 Hz, 3H), 5.21 (t, J=9.5 Hz, 1H), 5.14-5.09 (m, 5H), 5.08-4.97 (m, 5H), 4.16 (dt, J=6.5, 21.6 Hz, 3H), 4.06-4.00 (m, 7H), 3.75 (d, J=10.0 Hz, 1H), 3.68 (dd, J=4.2, 11.8 Hz, 3H), 3.59 (d, J=11.7 Hz, 1H), 3.55 (d, J=11.5 Hz, 1H), 2.16 (s, 3H), 2.10 (dd, J=3.5, 5.7 Hz, 13H), 2.08 (d, J=6.5 Hz, 8H), 2.01 (dd, J=3.3, 7.5 Hz, 17H), 2.00 (d, J=2.3 Hz, 7H), 1.98 (d, J=4.9 Hz, 8H), 1.95 (s, 7H). $^{13}$C NMR (200 MHz, CDCl$_3$) δ 170.8, 170.7, 170.6, 170.5, 170.42, 170.36, 170.3, 170.03, 169.99, 169.9, 169.8, 169.5, 169.4, 169.1, 169.0, 96.5, 96.2, 91.7, 89.0, 77.5, 77.4, 77.3, 77.1, 73.6, 73.1, 73.0, 70.6, 70.3, 70.0, 69.4, 69.1, 68.6, 68.4, 68.20, 68.17, 68.13, 68.08, 67.6, 67.5, 66.6, 66.5, 66.4, 65.9, 65.7, 61.9, 61.8, 21.2, 21.04, 20.92, 20.91, 20.87, 20.84, 20.82, 20.81, 20.80, 20.79, 20.78, 20.74, 20.72, 20.6. ESI-HRMS calcd. for $C_{28}H_{38}O_{19}$ [M+NH$_4$]$^+$: 696.2351. Found: 696.2315.

Example 4

Regioselective Acylation of Per-O-Silylated Trehalose

Per-O-TMS trehalose was selectively acylated as shown in Table 3. Trehalose contains two glucosyl moieties connected by an α-1,1 glycosidic bond. The symmetric disaccharide allows for the focused study of the reactivity of different hydroxyl groups without concerning the formation of c/13 anomers.

Per-O-TMS trehalose was prepared in one step from commercially available trehalose via known methods in quantitative yield and selectively acetylated starting with 4.0 equiv. of glacial acetic under microwave irradiation. After 0.5 h, the reaction mixture was purified to afford 6-monoacetate 16 and 6,6'-di-acetate 17 (Table 3, Entry 1). Longer reaction times (over 1.5 h) were needed to drive the reaction to completion when two equivalents of acid were used. After 1.5 h using 8 equivalents of acid, a distribution of penta-acetate 18, hexa-acetate 19, and per-acetate 20 was obtained (Table 3, Entry 2). Notably, the penta-acetate 18 and hexa-acetate 19 were two intermediates with both one glucosyl moiety fully acetylated, as observed by NMR. This interesting result suggested that once the 6 and 6' position were acetylated, one of the glucosyl moieties would be fully acetylated and lead to 6,2',3',4,6'-penta-acetate 18. Hexa-acetate 19 was also isolated in lower yield. Compound 18 had two un-acetylated TMS ether groups at the 2- and 3-positions, indicating the 4-position was slightly more reactive that the 2- and 3-positions.

TABLE 3

Selective acetylation of per-O-TMS trehalose.

per-O-TMS-trehalose $\xrightarrow[\text{temp., time}]{\text{Ac}_2\text{O, pyridine, AcOH}}$

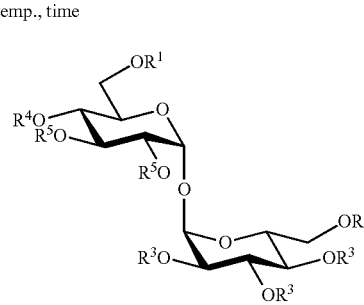

16. R$^1$ = Ac; R$^2$, R$^3$, R$^4$, R$^5$ = TMS
17. R$^1$, R$^2$ = Ac; R$^3$, R$^4$, R$^5$ = TMS
18. R$^1$, R$^2$, R$^3$ = Ac; R$^4$, R$^5$ = TMS
19. R$^1$, R$^2$, R$^3$, R$^4$ = Ac; R$^5$ = TMS
20. R$^1$, R$^2$, R$^3$, R$^4$, R$^5$ = Ac

| Entry | AcOH (equiv.) | Temp. | Time | Product Distribution (Yield) | | |
|---|---|---|---|---|---|---|
| 1 | 4 | μwave, 110° C. | 0.5 h | 16 (22%) | 17 (56%) | |
| 2 | 8 | μwave, 110° C. | 1.5 h | 18 (14%) | 19 (9%) | 20 (44%) |

Example 4.1

6-O-Acetyl-2,3,4,2',3',4',6'-hepta-O-trimethylsilyl-α,α-trehalose (16)

Following the general procedure described above, per-O-TMS trehalose (230 mg, 0.25 mmol) was acetylated using Ac$_2$O/pyridine and glacial acetic acid (57 μL, 1.00 mmol, 4.0 equiv.) followed by two microwave irradiation cycles (standard mode, 100 W, 110° C., ~40 psi, 15 min). The reaction mixture was purified using flash column chromatography (EA/Hex/NEt$_3$=5:95:5-EA/Hex=10:90) to afford compounds 16 and 17 (Table 3, Entry 1). Mono-acetylated analogue 16 (49 mg, 22%) was obtained as a white solid. TLC (EA/Hex=10:90) R$_f$ 0.53. $^1$H NMR (800 MHz, CDCl$_3$) δ 4.95 (d, J=3.1 Hz, 1H, H-1), 4.89 (d, J=3.1 Hz, 1H, H-1'), 4.24 (dd, J=11.9, 2.2 Hz, 1H, H-6a), 4.09 (dd, J=11.9, 4.5 Hz, 1H, H-6b), 4.01 (ddd, J=9.5, 4.4, 2.2 Hz, 1H, H-5), 3.91-3.88 (m, 2H, H-3, H-3'), 3.77 (dt, J=9.4, 3.1 Hz, H5'), 3.66 (d, J=3.1 Hz, 2H, H-6'ab), 3.48 (t, J=9.1 Hz, 1H, H-4), 3.46-3.41 (m, 2H, H-4', H-2), 3.39 (dd, J=9.3, 3.1 Hz, 1H, H-2'), 2.10 (s, 3H), 0.14 (s, 9H), 0.138 (s, 9H), 0.137 (s, 9H), 0.13 (s, 9H), 0.12 (s, 18H), 0.08 (s, 9H). $^{13}$C NMR (200 MHz, CDCl$_3$) δ 171.0, 94.4, 94.1, 73.5, 73.4, 73.3, 72.7, 72.6, 71.9, 71.5, 70.5, 21.0, 1.044, 1.040, 0.9, 0.8, 0.2, 0.1, −0.3. ESI-HRMS calcd. for $C_{35}H_{80}O_{12}Si_7$ [M+NH$_4$]$^+$: 906.4373. Found: 906.4385.

Example 4.2

6,6'-Di-O-acetyl-2,3,4,2',3',4'-hexa-O-trimethylsilyl-α,α-trehalose (17)

Di-acetylated analogue 17 (121 mg, 56%) was obtained as a white solid (Table 3, Entry 1). TLC (EA/Hex=1:9) R$_f$ 0.22. $^1$H NMR (800 MHz, CDCl$_3$) δ 4.93 (d, J=3.0 Hz, 2H, H-1, H-1'), 4.22 (dd, J=11.9, 2.2 Hz, 2H, H-6a, H-6'a), 4.08 (dd, J=11.9, 4.7 Hz, 2H, H-6b, H-6'b), 4.03-3.98 (m, 2H, H-5, H-5'), 3.90 (t, J=9.0 Hz, 2H, H-3, H-3'), 3.50-3.44 (m, 4H, H-2, H-2', H-4, H-4'), 2.09 (s, 6H), 0.14 (s, 18H), 0.14 (s, 18H), 0.12 (s, 18H). $^{13}$C NMR (200 MHz, CDCl$_3$) δ 170.9, 94.3, 73.4, 72.6, 71.9, 70.6, 63.7, 21.0, 1.0, 0.8, 1.2. ESI-HRMS calcd. for $C_{35}H_{80}O_{12}Si_7$ [M+NH$_4$]$^+$: 876.4083. Found: 876.4107.

Example 4.3

6,2',3',4',5',6'-Penta-O-Acetyl-2,3,4-tri-O-trimethylsilyl-α,α-trehalose (18)

Following the general procedure described above, per-O-TMS trehalose (230 mg, 0.25 mmol) was acetylated using Ac$_2$O/pyridine and glacial acetic acid (115 μL, 2.00 mmol, 8.0 equiv.) followed by three irradiation cycles (standard mode, 100 W, 110° C., ~40 psi, 30 min). The reaction mixture was purified using flash column chromatography (EA/Hex/NEt$_3$=30:70:5-EA/Hex=60:40) to afford compounds 18, 19, and 20 (Table 3, Entry 2). Penta-acetylated analogue 18 (26 mg, 14%) was obtained as a white amorphous foam. TLC (EA/Hex=7:3) R$_f$ 0.42. $^1$H NMR (800 MHz, CDCl$_3$) δ 5.54 (t, J=9.8 Hz, 1H, H-3), 5.23 (d, J=3.5 Hz, 1H, H-1), 5.14 (t, J=9.7 Hz, 1H, H-4), 4.99 (dd, J=10.3, 3.5 Hz, 1H, H-2), 4.92 (d, J=3.3 Hz, 1H, H-1'), 4.38-4.34 (m, 1H, H-5), 4.29 (dd, J=12.4, 3.6 Hz, 1H, H-6a), 4.19 (dd, J=11.7, 2.3 Hz, 1H, H-6'$_\alpha$), 4.10 (dd, J=11.8, 6.5 Hz, 1H, H-6'b), 4.01 (dd, J=12.4, 2.2 Hz, 1H, H-6b), 3.87 (t, J=9.0 Hz, 1H, H-3'), 3.83-3.78 (m, 1H, H-5'), 3.48 (dd, J=9.4, 3.3 Hz, 1H, H-2'), 3.41 (t, J=9.1 Hz, 1H, H-4'), 2.09 (s, 3H), 2.08 (s, 3H), 2.06 (s, 3H), 2.022 (s, 3H), 2.017 (s, 3H), 0.19 (s, 9H), 0.15 (s, 9H), 0.14 (s, 9H). $^{13}$C NMR (200 MHz, CDCl$_3$) δ 170.8, 170.7, 170.1, 169.8, 169.6, 95.8, 92.1, 73.4, 72.5, 72.1, 71.3, 70.2, 69.9, 68.2, 67.6, 63.4, 61.7, 20.8, 20.7, 20.6, 20.5, 1.1, 0.8, 0.2. ESI-HRMS calcd. for C$_{31}$H$_{56}$O$_{16}$Si$_3$ [M+NH$_4$]$^+$: 786.3214. Found: 786.3229.

Example 4.4

4,6,2',3',4',5',6'-Hexa-O-Acetyl-2,3,4-di-O-trimethyl-silyl-α,α-trehalose (19)

Hexa-acetylated analogue 19 (17 mg, 9%) was obtained as a white solid (Table 3, Entry 2). TLC (EA/Hex=3:7) R$_f$ 0.20. $^1$H NMR (600 MHz, CDCl$_3$) δ 5.56 (t, J=9.8 Hz, 1H, H-3'), 5.25 (d, J=3.5 Hz, 1H, H-1'), 5.16 (t, J=9.8 Hz, 1H, H-4'), 5.02 (dd, J=10.3, 3.6 Hz, 1H, H-2'), 4.98 (d, J=3.3 Hz, 1H, H-1), 4.89 (t, J=9.6 Hz, 1H, H-4), 4.37-4.29 (m, 2H, H-5', H-6'$_\alpha$), 4.21 (dd, J=12.7, 6.3 Hz, 1H, H-6a), 4.06-4.00 (m, 2H, H-3, H-6'b), 3.96-3.87 (m, 2H, H-5, H-6b), 3.62 (dd, J=9.2, 3.4 Hz, 1H, H-2), 2.10 (s, 3H), 2.10 (s, 3H), 2.07 (s, 3H), 2.06 (s, 3H), 2.04 (s, 3H), 0.15 (s, 9H), 0.14 (s, 9H). ESI-HRMS calcd. for C$_{30}$H$_{50}$O$_{17}$Si$_2$ [M+NH$_4$]$^+$: 756.2925. Found: 756.2938.

Example 4.5

2,3,4,6,2',3',4',5',6'-Octa-O-Acetyl-α,α-trehalose (20)

Per-O-acetylated analogue 20 (74 mg, 44%) was obtained as a white solid (Table 3, Entry 2). TLC (EA/Hex=1:1) R$_f$ 0.24. $^1$H NMR (800 MHz, CDCl$_3$) δ 5.48 (t, J=9.8 Hz, 2H, H-3, H-3'), 5.28 (d, J=3.7 Hz, 2H, H-1, H-1'), 5.05-5.01 (m, 4H, H-2, H-2', H-4, H-4'), 4.24 (dd, J=12.2, 5.7 Hz, 2H, H-6a, H-6'a), 4.04 (dt, J=19.8, 10.0 Hz, 2H, H-5, H-5'), 4.00 (dd, J=12.2, 2.0 Hz, 2H, H-6b, H-6'b), 2.08 (s, 6H), 2.07 (s, 6H), 2.04 (s, 6H), 2.03 (s, 6H). $^{13}$C NMR (200 MHz, CDCl$_3$) 170.6, 170.0, 169.6, 169.5, 92.2, 69.9, 69.9, 68.5, 68.1, 61.7, 20.7, 20.6, 20.5. ESI-HRMS calcd. for C$_{28}$H$_{38}$O$_{19}$ [M+Na]$^+$: 701.1900. Found: 701.1898.

Example 5

Selective Acetylation of Per-O-Cellobiose

Selective Acetylation of Per-O-TMS-Cellobiose

Per-O-trimethylsilylcellobiose (107 mg, 0.116 mmol) was acetylated with 7 equivalents of glacial acetic acid under microwave irradiation for 25 min to afford 6,6'-di-O-acetyl-1,2,2',3,3',4'-hexakis-O-trimethylsilylcellobiose (17 mg, 17%) and 1,6,6'-tri-O-acetyl-2,2',3,3',4'-pentakis-O-trimethylsilylcellobiose (44 mg, 45%). A summary of the selective acetylation of per-O-TMS cellobiose is set forth in Table 4.

TABLE 4

Selective acetylation of per-O-TMS cellobiose.

| Entry | AcOH (eq) | Temp | Time | Product Distribution/Yield | |
|---|---|---|---|---|---|
| 1 | 3 | μwave, 110° C. | 75 min | 1 (10%) | 2 (16%) |
| 2 | 3 | μwave, 110° C. | 150 min | 1 (20%) | 2 (36%) |
| 3 | 7 | μwave, 110° C. | 25 min | 1 (17%) | 2 (45%) |

Example 5.1

1,2,2',3,3',4',6,6'-octakis-O-trimethylsilylcellobiose

Colorless oily solid; $^1$H NMR (800 MHz, CDCl3) δ 4.45 (1H, d, J=7.4 Hz, H-1) 4.35 (1H, d, J=7.7 Hz, H-1) 3.85 (1H, dd, J=3.7, 11.0 Hz, H-6a) 3.79 (2H, m, H-6b & H-6a') 3.75 (1H, app. t, J=8.8 Hz, H-4) 3.56 (1H, dd, J=6.1, 10.9 Hz, H-6b') 3.43 (1H, app. t, J=8.8 Hz, H-3) 3.31 (1H, app. t, J=8.8 Hz, H-3') 3.27 (1H, app. t, J=8.8 Hz, H-4') 3.24 (2H, m, H-2 & H-2') 3.20 (1H, m, H-5) 3.11 (1H, m, H-5') 0.16 (9H, s, TMS) 0.15 (9H, s, TMS) 0.14 (9H, s, TMS) 0.14 (9H, s, TMS) 0.13 (9H, s, TMS) 0.13 (18H, s, TMS) 0.12 (9H, s, TMS). $^{13}$C NMR (200 mHz, CDCl$_3$): δ 101.4, 98.4, 78.4, 77.9, 77.7, 76.6, 76.0, 75.2, 74.3, 72.1, 60.9, 1.5, 1.5, 1.4, 1.2, 0.6, 0.0, −0.3. HRMS: (ESI-MS m/z) calc. mass for C$_{36}$H$_{86}$O$_{11}$Si$_8$ [M+NH$_4$]$^+$, 936.4668. found 936.4689.

Example 5.2

6,6'-di-O-acetyl-1,2,2',3,3',4'-hexakis-O-trimethylsilylcellobiose

Colorless oil; R$_f$=0.60 in 4:1 hexane/EtOAc; $^1$H NMR (800 MHz, CDCl3) δ 4.49 (1H, d, J=11.2 Hz, H-6a) 4.45 (1H, d, J=8.0 Hz, H-1) 4.30 (1H, dd, J=3.2, 12.0 Hz, H-6a) 4.27 (1H, dd, J=5.6, 12.0 Hz, H-6b) 4.08 (1H, d, J=7.2 Hz, H-1) 4.07 (1H, dd, J=4.8, 12.0 Hz, H-6b) 3.45 (4H, m, H-3, H-4, H-4' & H-5) 3.32 (2H, m, H-3 & H-5) 3.26 (1H, app. t, J=8.0 Hz, H-2) 3.22 (1H, app. t, J=8.0 Hz, H-2) 2.06 (3H, s, Ac) 2.05 (3H, s, Ac) 0.15 (9H, s, TMS) 0.15 (9H, s, TMS) 0.14 (9H, s, TMS) 0.13 (9H, s, TMS) 0.13 (9H, s, TMS) 0.10 (9H, s, TMS). $^{13}$C NMR (200 mHz, CDCl$_3$): δ 170.8, 170.5, 102.7, 97.9, 77.7, 77.5, 76.8, 75.7, 74.4, 73.9, 73.2, 71.6, 63.6, 62.7, 20.9, 20.9, 1.3, 1.0, 1.0, 1.0, 0.9, 0.2. HRMS: (ESI-MS m/z) calc. mass for C$_{34}$H$_{78}$NO$_{13}$Si$_6$ [M+Na]$^+$, 881.3643. found 881.3633.

Example 5.3

α-1,6,6'-tri-O-acetyl-2,2',3,3',4'-pentakis-O-trimethylsilylcellobiose

Colorless oil; $R_f$=0.50 in 4:1 hexane/EtOAc; $^1$H NMR (800 MHz, CDCl3) δ 6.07 (1H, d, J=3.7 Hz, H-1) 4.42 (1H, dd, J=4.0, 12.0 Hz, H-6a) 4.38 (1H, dd, J=2.4, 12.0 Hz, H-6b) 4.33 (1H, dd, J=2.4, 12.0 Hz, H-6a') 4.10 (1H, d, J=8.0 Hz, H-1') 4.07 (1H, dd, J=4.0, 11.2 Hz, H-6b') 3.88 (1H, m, H-5) 3.73 (1H, app. t, J=8.8 Hz, H-3) 3.61 (1H, dd, J=3.2, 8.8 Hz, H-2) 3.57 (1H, app. t, j=8.8 Hz, H-4) 3.49 (1H, app. t, J=8.8 Hz, H-4') 3.32 (1H, app. t, J=8.8 Hz, H-3') 3.30 (1H, m, H-5') 3.22 (1H, app. t, J=8.0 Hz, H-2') 2.13 (3H, s, Ac) 2.09 (3H, s, Ac) 2.07 (3H, s, Ac) 0.16 (9H, s, TMS) 0.15 (9H, s, TMS) 0.14 (9H, s, TMS) 0.11 (18H, s, TMS). $^{13}$C NMR (200 mHz, CDCl$_3$): δ 170.7, 170.4, 169.3, 102.7, 91.7, 77.4, 76.8, 74.4, 73.9, 72.4, 72.1, 71.4, 71.1, 63.4, 62.1, 20.9, 20.9, 1.3, 1.0, 0.8, 0.7, 0.0. HRMS: (ESI-MS m/z) calc. mass for $C_{33}H_{68}O_{14}Si_5$ [M+NH$_4$]$^+$, 846.3799. found 846.3807.

Example 5.4

β-1,6,6'-tri-O-acetyl-2,2',3,3',4'-pentakis-O-trimethylsilylcellobiose

Colorless oil; $R_f$=0.46 in 4:1 hexane/EtOAc; $^1$H NMR (800 MHz, CDCl3) δ 5.42 (1H, d, J=8.0 Hz, H-1) 4.42 (1H, d, J=12.0 Hz, H-6a) 4.37 (1H, dd, J=4.8, 12.0 Hz, H-6b) 4.32 (1H, d, J=12.0 Hz, H-6a') 4.09 (1H, dd, J=8.0, 12.0 Hz, H-6b') 4.07 (1H, d, J=8.0 Hz, H-1') 3.61 (1H, m, H-5) 3.56 (1H, app. t, J=8.8 Hz, H-4) 3.52 (1H, app. t, J=8.8 Hz, H-?) 3.48 (1H, app. t, j=8.8 Hz, H-?) 3.45 (1H, app. t, J=8.8 Hz, H-4') 3.28 (1H, app. t, J=8.8 Hz, H-3') 3.30 (1H, m, H-5') 3.22 (1H, app. t, J=8.8 Hz, H-2') 2.13 (3H, s, Ac) 2.08 (3H, s, Ac) 2.07 (3H, s, Ac) 0.16 (9H, s, TMS) 0.14 (18H, s, TMS) 0.14 (9H, s, TMS) 0.12 (9H, s, TMS). $^{13}$C NMR (200 mHz, CDCl$_3$): δ 170.7, 170.4, 169.3, 102.6, 94.0, 77.5, 76.6, 75.9, 74.2, 74.0, 73.9, 71.5, 63.5, 62.2, 21.3, 20.9, 1.2, 1.0, 0.9, 0.8, 0.8. HRMS: (ESI-MS m/z) calc. mass for $C_{33}H_{68}O_{14}Si_5$ [M+NH$_4$]$^+$, 846.3799. found 846.3810.

Example 6

Selective Acylation of Per-O-Trimethylsilyltrehalose

Selective Acetylation of per-O-TMS-trehalose. Per-O-trimethylsilyltrehalose (460 mg, 0.5 mmol) was acetylated with varying amounts of glacial acetic acid under microwave irradiation to afford 6-O-acetyl-2,2',3,3',4,4',6'-heptakis-O-trimethylsilyltrehalose and 6,6'-di-O-acetyl-2,2',3,3',4,4'-hexakis-O-trimethylsilyltrehalose.

A summary of the selective acetylation of per-O-TMS trehalose is set forth in Table 5.

TABLE 5

Selective acetylation of per-O-TMS trehalose.

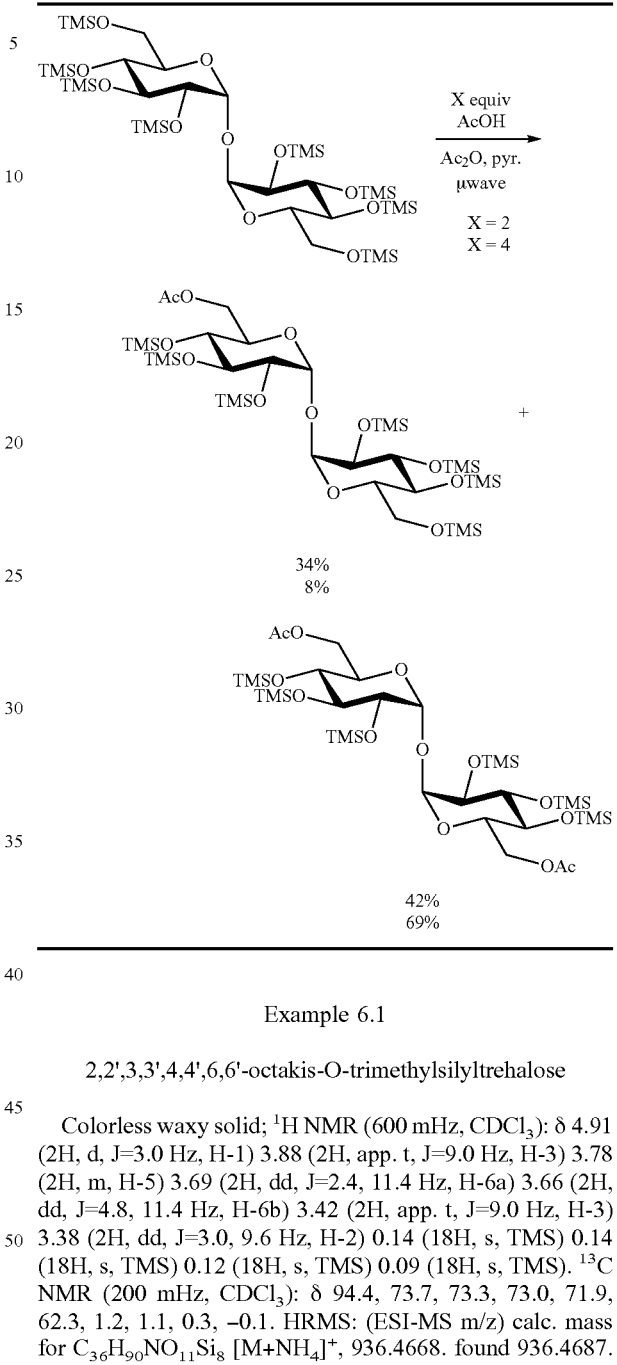

Example 6.1

2,2',3,3',4,4',6,6'-octakis-O-trimethylsilyltrehalose

Colorless waxy solid; $^1$H NMR (600 mHz, CDCl$_3$): δ 4.91 (2H, d, J=3.0 Hz, H-1) 3.88 (2H, app. t, J=9.0 Hz, H-3) 3.78 (2H, m, H-5) 3.69 (2H, dd, J=2.4, 11.4 Hz, H-6a) 3.66 (2H, dd, J=4.8, 11.4 Hz, H-6b) 3.42 (2H, app. t, J=9.0 Hz, H-3) 3.38 (2H, dd, J=3.0, 9.6 Hz, H-2) 0.14 (18H, s, TMS) 0.14 (18H, s, TMS) 0.12 (18H, s, TMS) 0.09 (18H, s, TMS). $^{13}$C NMR (200 mHz, CDCl$_3$): δ 94.4, 73.7, 73.3, 73.0, 71.9, 62.3, 1.2, 1.1, 0.3, −0.1. HRMS: (ESI-MS m/z) calc. mass for $C_{36}H_{90}NO_{11}Si_8$ [M+NH$_4$]$^+$, 936.4668. found 936.4687.

Example 6.2

6-O-acetyl-2,2',3,3',4,4',6'-heptakis-O-trimethylsilyltrehalose

Colorless solid; $R_f$=0.73 in 4:1 hexane/EtOAc; $^1$H NMR (800 MHz, CDCl$_3$) δ 4.95 (1H, d, J=3.1 Hz, H-1) 4.89 (1H, d, J=3.1 Hz, H-1) 4.24 (1H, dd, J=2.2, 11.9 Hz, H-6a) 4.09 (1H, dd, J=4.5, 11.9 Hz, H-6b) 4.01 (1H, m, H-5) 3.91 (1H, app. t, J=11.2 Hz, H-3) 3.88 (1H, app. t, J=11.2 Hz, H-3) 3.77 (1H, m, H-5') 3.66 (2H, d, J=3.1 Hz, H-6'a&b) 3.45 (3H, m, H-2, H-4 & H-4') 3.40 (1H, dd, J=3.0, 9.6 Hz, H-2)

2.01 (3H, s, Ac) 0.15 (9H, s, Ac) 0.14 (18H, s, Ac) 0.13 (9H, s, Ac) 0.13 (9H, s, Ac) 0.12 (9H, s, Ac) 0.09 (9H, s, Ac). $^{13}$C NMR (200 mHz, CDCl$_3$): δ 171.0, 94.4, 94.1, 73.4, 73.4, 73.3, 72.7, 72.5, 71.8, 71.5, 70.4, 63.7, 61.9, 21.0, 1.0, 0.9, 0.8, 0.2, 0.1, −0.3. HRMS: (ESI-MS m/z) calc. mass for C$_{35}$H$_{84}$NO$_{12}$Si$_7$ [M+NH$_4$]$^+$, 906.4378. found 936.4385.

Example 6.3

6,6'-di-O-acetyl-2,2',3,3',4,4'-hexakis-O-trimethylsilyltrehalose

Colorless powder; R$_f$=0.50 in 4:1 hexane/EtOAc; $^1$H NMR (600 mHz, CDCl$_3$): δ 4.93 (2H, d, J=2.4 Hz, H-1) 4.22 (2H, dd, J=2.4, 12.0 Hz, H-6a) 4.08 (2H, dd, J=4.8, 12.0 Hz, H-6b) 4.00 (2H, m, H-5) 3.90 (2H, app.t, J=8.8 Hz, H-3) 3.48 (2H, app.t, J=8.8 Hz, H-4) 3.46 (2H, dd, J=3.2, 8.8 Hz, H-2) 2.09 (6H, s, Ac) 0.15 (18H, s, TMS) 0.13 (18H, s, TMS) 0.12 (18H, s, TMS). $^{13}$C NMR (200 mHz, CDCl$_3$): δ 171.0, 94.3, 73.4, 72.5, 71.8, 70.6, 63.7, 21.0, 1.0, 0.8, 0.1. HRMS: (ESI-MS m/z) calc. mass for C$_{34}$H$_{78}$NO$_{13}$Si$_6$ [M+NH$_4$]$^+$, 876.4089. found 876.4107.

Example 6.4

2,3,4,6,6'-penta-O-acetyl-2',3',4'-tris-O-trimethylsilyltrehalose

Colorless oil; R$_f$=0.40 in 7:3 hexane/EtOAc; $^1$H NMR (600 mHz, CDCl$_3$): δ 5.55 (1H, app.t, J=9.6 Hz, H-3) 5.24 (1H, d, J=3.6 Hz, H-1) 5.14 (1H, app.t, J=9.6 Hz, H-4) 4.99 (1H, dd, J=3.6, 10.2 Hz, H-2) 4.93 (1H, d, J=2.4 Hz, H-1') 4.36 (1H, m, H-5) 4.29 (1H, dd, J=3.6, 12.0 Hz, H-6a) 4.20 (1H, dd, J=2.4, 12.0 Hz, H-6a') 4.10 (1H, dd, J=6.0, 12.0 Hz, H-6b') 4.02 (1H, dd, J=2.4, 12.0 Hz, H-6b) 3.87 (1H, app.t, J=9.0 Hz, H-3') 3.80 (1H, m, H-5) 3.49 (1H, dd, J=3.0, 9.0 Hz, H-2) 3.41 (1H, app.t, J=9.0 Hz, H-4) 2.09 (3H, s, Ac) 2.08 (3H, s, Ac) 2.07 (3H, s, Ac) 2.02 (3H, s, Ac) 2.02 (3H, s, Ac) 0.20 (9H, s, TMS) 0.16 (9H, s, TMS) 0.15 (9H, s, TMS). $^{13}$C NMR (200 mHz, CDCl$_3$): δ 171.0. HRMS: (ESI-MS m/z) calc. mass for C$_{31}$H$_{60}$NO$_{16}$Si$_3$ [M+NH$_4$]$^+$, 786.3220. found 786.3229.

Example 6.5

2,3,4,4',6,6'-hexa-O-acetyl-2',3'-bis-O-trimethylsilyltrehalose

Colorless oil; R$_f$=0.20 in 7:3 hexane/EtOAc; $^1$H NMR (600 MHz, CDCl$_3$) δ 5.56 (1H, app. t, J=9.8 Hz, H-3) 5.25 (1H, d, J=3.5 Hz, H-1) 5.16 (1H, app. t, J=9.8 Hz, H-4) 5.02 (1H, dd, J=3.6, 10.3 Hz, H-2) 4.98 (1H, d, J=3.3 Hz, H-1') 4.89 (1H, t, J=9.6 Hz, H-3') 4.32 (2H, m, H-5 & H-6a) 4.21 (1H, dd, J=6.3, 12.7 Hz, H-6a') 4.02 (2H, m, H-3' & H-6b) 3.90 (2H, m, H-5' & H-6b') 3.62 (1H, dd, J=3.4, 9.2 Hz, H-2') 2.10 (3H, s, Ac) 2.10 (3H, s, Ac) 2.07 (3H, s, Ac) 2.06 (3H, s, Ac) 2.04 (3H, s, Ac) 0.16 (9H, s, TMS) 0.15 (9H, s, TMS). $^{13}$C NMR (200 mHz, CDCl$_3$): δ 170.9, 170.8, 170.5, 169.7, 169.7, 95.9, 92.5, 72.7, 71.7, 70.9, 70.4, 70.1, 69.1, 68.3, 67.9, 62.5, 61.7, 21.3, 20.9, 20.9, 20.8, 20.7, 20.7, 0.8, 0.4. HRMS: (ESI-MS m/z) calc. mass for C$_{30}$H$_{54}$NO$_{17}$Si$_2$ [M+NH$_4$]$^+$, 756.2930. found 756.2938.

Example 6.6

2,3,4,2',3',6,6'-hepta-O-acetyl-4'-O-trimethylsilyltrehalose

Colorless oil; R$_f$=in 7:3 hexane/EtOAc; $^1$H NMR (800 MHz, CDCl$_3$) δ 5.47 (1H, app. t, J=9.6 Hz, H-3) 5.41 (1H, app. t, J=9.6 Hz, H-3') 5.27 (1H, d, J=3.2 Hz, H-1) 5.19 (1H, d, J=3.2, H-1') 5.04 (1H, app. t, J=9.6 Hz, H-4) (1H, dd, J=3.2, 10.4 Hz, H-2) 4.94 (1H, dd, J=3.2, 10.4 Hz, H-2') 4.20 (3H, m, H-6a, H-6a' & H-6b') 4.08 (1H, m, H-5) 3.98 (1H, d, J=12.0 Hz, H-6b) 3.92 (1H, m, H-5') 3.75 (1H, app. t, J=9.6, H-4') 2.10 (6H, s, Ac) 2.08 (3H, s, Ac) 2.07 (3H, s, Ac) 2.06 (3H, s, Ac) 2.05 (3H, s, Ac) 2.02 (3H, s, Ac) 0.11 (9H, s, TMS). $^{13}$C NMR (200 mHz, CDCl$_3$): δ 170.6, 170.6, 169.9, 169.8, 169.7, 169.6, 169.5, 92.6, 92.2, 72.3, 70.4, 70.3, 69.9, 69.7, 69.6, 68.4, 67.9, 62.4, 61.7, 21.1, 20.7, 20.6, 20.6, 20.6, 20.6, 0.2. HRMS: (ESI-MS m/z) calc. mass for C$_{29}$H$_{48}$NO$_{18}$Si [M+NH$_4$]$^+$, 726.2641. found 726.2642.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A selectively-acylated oligosaccharide selected from the group consisting of:

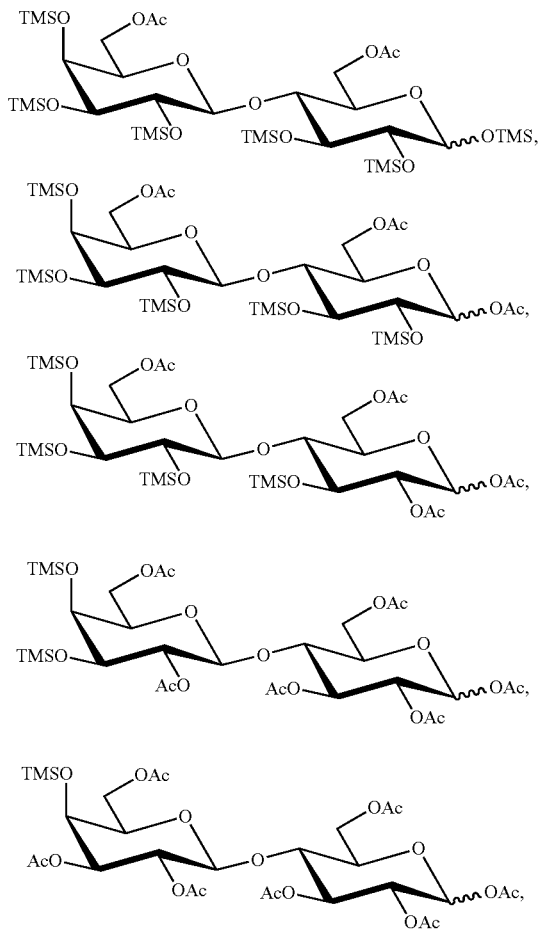

-continued

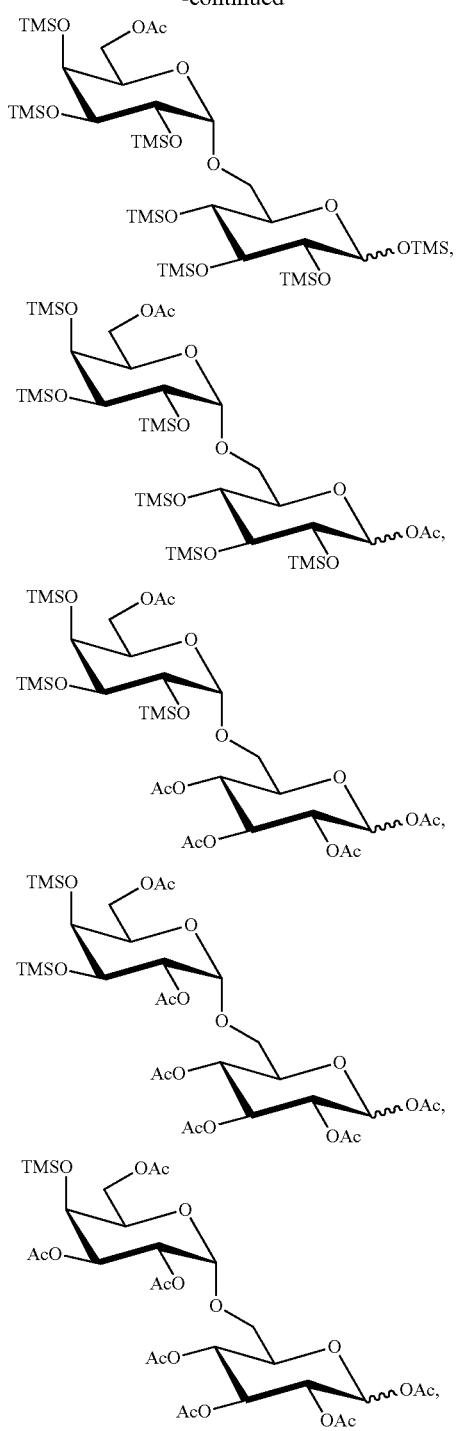

-continued

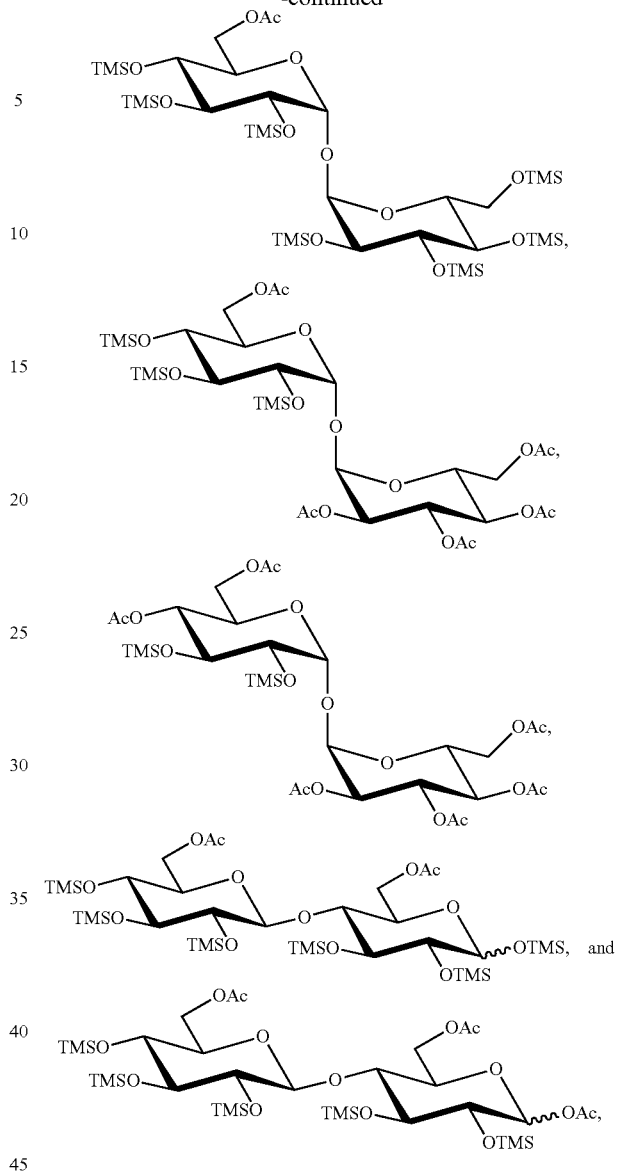

wherein each TMS is Si(Me)$_3$ and each Ac is C(O)Me.

2. A method for preparing a selectively-acylated oligosaccharide according to claim 1, the method comprising forming a reaction mixture comprising a per-O-trimethylsilyl oligosaccharide and an acylating agent, wherein
the acylating agent is acetic anhydride, and
the reaction mixture is formed under conditions sufficient to selectively replace at least one trimethylsilyl group with a —C(O)Me group,
thereby preparing the selectively-acylated oligosaccharide.

* * * * *